United States Patent
Newell-Rogers et al.

(10) Patent No.: US 9,359,404 B2
(45) Date of Patent: Jun. 7, 2016

(54) METHODS AND PRODUCTS FOR TREATING PREECLAMPSIA AND MODULATING BLOOD PRESSURE

(71) Applicants: Scott & White Healthcare, Temple, TX (US); The Texas A&M University System, College Station, TX (US); Viral Genetics, Inc., San Marino, CA (US)

(72) Inventors: Martha Karen Newell-Rogers, Holland, TX (US); Brett Mitchell, Belton, TX (US); Evan Newell, Singapore (SG)

(73) Assignees: Scott & White Healthcare, Temple, TX (US); The Texas A&M University System, College Station, TX (US); VG Life Sciences, Inc., Santa Barbara, CA (US)

(*) Notice: Subject to any disclaimer, the term of this patent is extended or adjusted under 35 U.S.C. 154(b) by 0 days.

(21) Appl. No.: 14/362,157

(22) PCT Filed: Nov. 30, 2012

(86) PCT No.: PCT/US2012/067364
§ 371 (c)(1),
(2) Date: Jun. 2, 2014

(87) PCT Pub. No.: WO2013/082472
PCT Pub. Date: Jun. 6, 2013

(65) Prior Publication Data
US 2014/0315818 A1    Oct. 23, 2014

Related U.S. Application Data

(60) Provisional application No. 61/565,952, filed on Dec. 1, 2011.

(51) Int. Cl.
*C07K 7/06*       (2006.01)
*C12N 15/113*     (2010.01)
*A61K 38/08*      (2006.01)
*A61K 38/10*      (2006.01)

(52) U.S. Cl.
CPC . *C07K 7/06* (2013.01); *A61K 38/08* (2013.01); *A61K 38/10* (2013.01); *C12N 15/113* (2013.01)

(58) Field of Classification Search
None
See application file for complete search history.

(56) References Cited

U.S. PATENT DOCUMENTS

| 5,616,554 | A  | 4/1997  | Beardsley    |
| 8,557,764 | B2 | 10/2013 | Newell et al. |
| 8,906,846 | B2 | 12/2014 | Newell et al. |
| 8,957,031 | B2 | 2/2015  | Newell et al. |
| 2004/0018639 | A1 | 1/2004 | Zhabilov |
| 2009/0175838 | A1 | 7/2009 | Newell Rogers et al. |
| 2010/0034839 | A1 | 2/2010 | Newell et al. |
| 2010/0166782 | A1 | 7/2010 | Newell et al. |
| 2010/0166789 | A1 | 7/2010 | Keledjian et al. |
| 2011/0118175 | A1 | 5/2011 | Newell et al. |
| 2013/0259829 | A1 | 10/2013 | Newell et al. |
| 2013/0295047 | A1 | 11/2013 | Newell et al. |
| 2014/0220000 | A1 | 8/2014 | Newell et al. |

FOREIGN PATENT DOCUMENTS

| WO | WO 98/18491 A1   | 5/1998  |
| WO | WO 2004/043361 A2 | 5/2004 |
| WO | WO 2005/079523 A2 | 9/2005 |
| WO | WO 2008/054635 A2 | 5/2008 |
| WO | WO 2012/094495 A2 | 7/2012 |

OTHER PUBLICATIONS

Adams et al., Biological activity and therapeutic potential of homologs of an Ii peptide which regulates antigenic peptide binding to cell surface MHC class II molecules. Arzneimittelforschung. Sep. 1997;47(9):1069-77.

Ayala-Gaytan et al., Diminution of plasma viral load and cultured HIV-infected peripheral blood mononuclear cells in non-responding patients treated with two calf thymus nuclear proteins and conventional antiretrovirals. HIV AIDS Rev. 2004;3(3):8-13.

Barrera et al., The role of the invariant chain in mucosal immunity. Int Arch Allergy Immunol. Oct. 1998;117(2):85-93.

Cantin et al., A novel virus capture assay reveals a differential acquisition of host HLA-DR by clinical isolates of human immunodeficiency virus type 1 expanded in primary human cells depending on the nature of producing cells and the donor source. J Gen Virol. Dec. 2001;82(Pt 12):2979-87.

Gunther et al., Bidirectional binding of invariant chain peptides to an MHC class II molecule. Proc Natl Acad Sci U S A. Dec. 21, 2010;107(51):22219-24. Epub Nov. 29, 2010.

Hillman et al., Generating MHC Class II+/Ii−phenotype after adenoviral delivery of both an expressible gene for MHC Class II inducer and an antisense Ii-RNA construct in tumor cells. Gene. Ther. Aug. 2003;10(17):1512-8.

Hitzel et al., The invariant chain derived fragment CLIP is an efficient in vitro inhibitor of peptide binding to MHC class II molecules. Mol Immunol. Jan. 1996;33(1):25-31.

Kasai et al., CLIP-derived self-peptides bound to MHC class II molecules of medullary thymic epithelial cells differ from those of cortical thymic epithelial cells in their diversity, length, and C-terminal processing. Eur J Immunol. Dec. 2000;30(12):3542-51.

Lu et al., Suppression of major histocompatibility complex class II-associated invariant chain enhances the potency of an HIV gp120 DNA vaccine. Immunology. Feb. 2007;120(2):207-16.Epub Nov. 20, 2006.

(Continued)

*Primary Examiner* — Thomas S Heard
(74) *Attorney, Agent, or Firm* — Wolf, Greenfield & Sacks, P.C.

(57) ABSTRACT

The invention relates to methods for altering biological parameters in a subject, such as reducing blood pressure in a subject, by displacing CLIP, using a CLIP inhibitor. The methods are useful for treating disorders such as preeclampsia and high blood pressure.

13 Claims, 15 Drawing Sheets

(56) References Cited

OTHER PUBLICATIONS

Mozes et al., A novel synthetic peptide for the specific treatment of lupus: clinical effects and mechanism of action. Isr Med Assoc J. Jan. 2008;10(1):40-2.

Newell et al., Biochemical characterization of proteins that co-purify with class II antigens of the murine MHC. J Immunol. Mar. 15, 1988;140(6):1930-8.

Newell et al., Chloroquine affects biosynthesis of Ia molecules by inhibiting dissociation of invariant (gamma) chains from alpha-beta dimers in B cells. J Exp Med. Oct. 1, 1985;162(4):1371-6.

Newell et al., TLR-mediated B cell activation results in ectopic CLIP expression that promotes B cell-dependent inflammation. J Leukoc Biol. Oct. 2010;88(4):779-89. Epub Jul. 14, 2010.

Noveljic et al., Virological responses of treatment-naïve stage CDC-2 HIV-1 positive subjects receiving VGV-1 injections in a blinded, placebo-controlled, multi-centre clinical trial. Retrovirology. 2006; 3(Suppl 1): p. 73.

Powis, CLIP-region mediated interaction of Invariant chain with MHC class I molecules. FEBS Lett. May 29, 2006;580(13):3112-6. Epub Apr. 27, 2006.

Roberts et al., Host protein incorporation is conserved among diverse HIV-1 subtypes. AIDS. Feb. 25, 1999;13(3):425-7.

Schindler et al., Down-modulation of mature major histocompatibility complex class II and up-regulation of invariant chain cell surface expression are well-conserved functions of human and simian immunodeficiency virus nef alleles. J Virol. Oct. 2003;77(19):10548-56.

Stumptner et al., Interaction of MHC class II molecules with the invariant chain: role of the invariant chain (81-90) region. EMBO J. Oct. 1, 1997;16(19):5807-18.

Wu et al., The MHC class II-associated invariant chain-derived peptide clip binds to the peptide-binding groove of class II molecules. Mol Immunol. Mar.-Apr. 1996;33(4-5):371-7.

Xu et al, Immunotherapy of cancer by antisense inhibition of Ii protein, an immunoregulator of antigen selection by MHC class II molecules. Curr Opin Mol Ther. Apr. 2004;6(2):160-5.

METHODS AND PRODUCTS FOR TREATING PREECLAMPSIA AND MODULATING BLOOD PRESSURE

BACKGROUND OF INVENTION

Preeclampsia is a complication of pregnancy that is believed to be responsible for 20% of pregnancy-related maternal deaths and 10% of all premature births. Preeclampsia can cause fetal growth restriction, fetal death and morbidity, premature deliveries, and death of the mother. Its symptoms typically become evident after the 20th week of pregnancy.

Preeclampsia is typically diagnosed after symptoms have developed by detecting high blood pressure of a pregnant woman or by checking her urine for protein. Specifically, preeclampsia is diagnosed when a pregnant woman develops high blood pressure (two separate readings taken at least four hours apart of 140/90 mm Hg or more) and 300 mg of protein in a 24-hour urine sample (i.e., proteinuria). Currently, there are no tests for predicting preeclampsia or for determining the severity of the condition that may develop. Additionally, no treatments are currently available to cure preeclampsia. The current therapeutic approach to preeclampsia involves monitoring the severity of the disorder and ending the pregnancy, either by induction of labor or cesarean before the symptoms become too severe.

SUMMARY OF INVENTION

The invention is based at least in part on the discovery that modulation of CLIP on a cell surface provides a mechanism for controlling blood pressure and other biological responses in response to various disease conditions and also for treating preeclampsia. It has been found that CLIP in the groove of MHC class II can directly prevent MHC-mediated cell death. Therefore agents that displace CLIP from MHC expressing cells or otherwise prevent CLIP from associating with MHC are useful for the treatment of a variety of diseases including preeclampsia and high blood pressure associated with heart disease.

In one aspect the invention is a method of treating a subject having preeclampsia, by administering to the subject an isolated CLIP inhibitor in an effective amount to reduce the blood pressure in the subject with respect to blood pressure levels prior to treatment.

In another aspect, the invention is a method for administering to a subject having high blood pressure an isolated CLIP inhibitor in an effective amount to reduce the blood pressure in the subject with respect to blood pressure levels prior to treatment. In some embodiments the subject has heart disease.

In some embodiments the CLIP inhibitor is synthetic. In other embodiments the CLIP inhibitor is a TNP peptide, an siRNA, or an MHC class II CLIP inhibitor. In yet other embodiments the CLIP inhibitor comprises a peptide having the sequence: $X_1RX_2X_3X_4X_5LX_6X_7$ (SEQ ID NO: 3), wherein each X is an amino acid, wherein R is Arginine, L is Leucine and wherein at least one of X2 and X3 is Methionine, wherein the peptide is not N-MRMATPLLM-C (SEQ ID NO: 1), and wherein the peptide is a CLIP displacer. The peptide in some embodiments has any one or more of the following variables: $X_1$ is Phenylalanine; $X_2$ is Isoleucine; $X_3$ is Methionine; $X_4$ is Alanine; $X_5$ is Valine; $X_6$ is Alanine; and/or $X_7$ is Serine.

The peptide in some embodiments includes 1-5 amino acids at the N and/or C terminus. For instance, the peptide may have 1-5 amino acid at the C terminus of $X_1RX_2X_3X_4X_5LX_6X_7$ (SEQ ID NO: 3) and/or the peptide may have 1-5 amino acid at the N terminus of $X_1RX_2X_3X_4X_5LX_6X_7$ (SEQ ID NO: 3).

The peptide in other embodiments comprises FRIM $X_4VLX_6S$ (SEQ ID NO: 6), wherein $X_4$ and $X_6$ are any amino acid. Optionally $X_4$ and $X_6$ are Alanine.

In some embodiments the peptide comprises FRIMAVLAS (SEQ ID NO: 2), IRIMATLAI (SEQ ID NO: 4), FRIMAVLAI (SEQ ID NO: 10), or IRIMAVLAS (SEQ ID NO: 11) or combinations thereof.

The peptide in some embodiments has 9-20 amino acids.

In other embodiments the CLIP inhibitor comprises a peptide selected based on the subject's HLA-DR allele.

In another aspect the invention is a composition comprising IRIMATLAI (SEQ ID NO: 4).

In another aspect the invention is a composition comprising FRIMAVLAI (SEQ ID NO: 10).

In yet another aspect the invention is a composition comprising IRIMAVLAS (SEQ ID NO: 11).

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 8A examines CD3 and CD25 levels on control or pregnant (P) mice treated with R837, CLO097 (Clo) or poly I:C (PIC) but without TPP. FIG. 8B examines CD3 and CD25 levels on pregnant (P) mice treated with TPP, R837 and/or TPP, CLO097 (Clo) and/or TPP or poly I:C (PIC) and/or TPP (the two graphs depict the results of two separate experiments).

FIG. 9C is a graph that shows a significant increase in CLIP+B cells with Poly I:C in pregnant mice that is reversed with TPP.

FIG. 11A. Splenic levels of CLIP+T cells were increased significantly in PE mice (PPIC and PR) compared to vehicle-treated pregnant controls (P). FIG. 11B. A decrease in splenic B cells was observed in normal pregnant mice (P), which was absent in PE mice (PPIC). Splenocytes were analyzed by flow cytometry.

DETAILED DESCRIPTION

Figure 1:
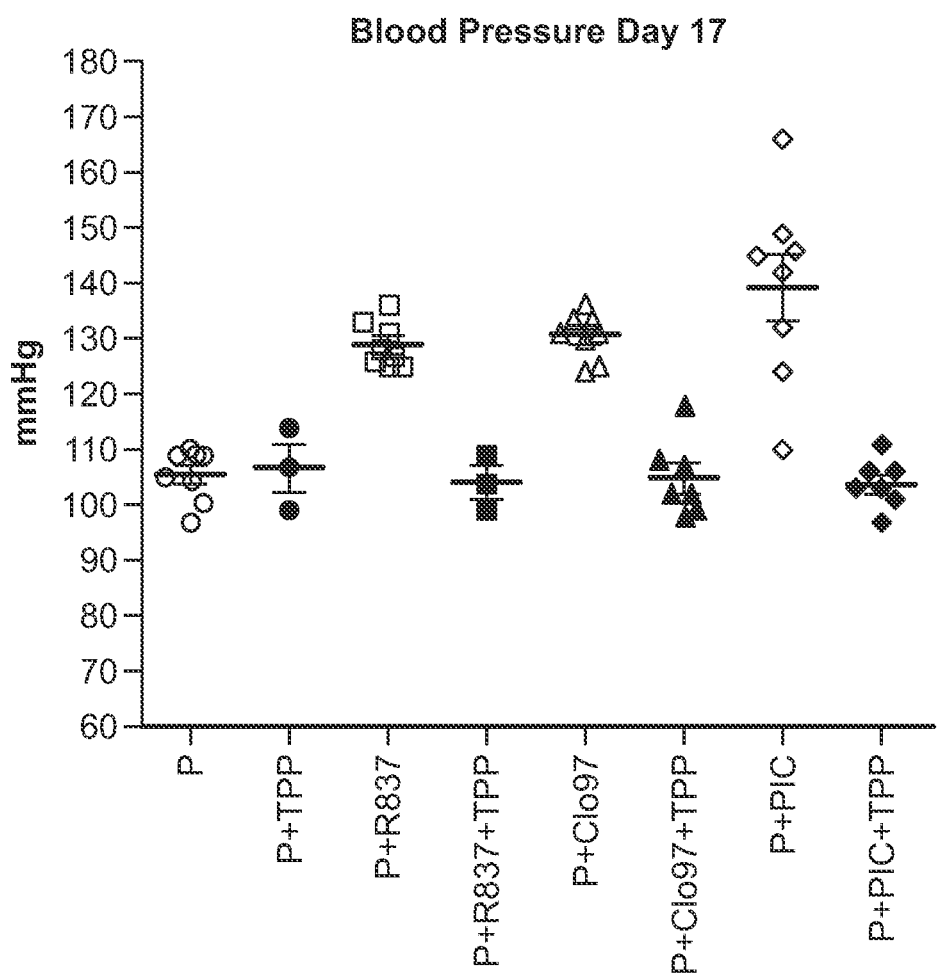
FIG. 1 is a graph depicting the effects of TLR agonists with or without a CLIP inhibitor on blood pressure in pregnant mice. Pregnant mice (P) were treated with one of three TLR agonists to induce a physiological condition which mimics preeclampsia, Poly I:C (PIC), R837 or CLO097. Control pregnant mice received vehicle or vehicle plus TPP (peptide of SEQ ID NO: 5). The blood pressure of each mouse was measured on day 17 following treatment.

When a B cell is activated non-specifically, it expresses an important, small self-peptide called MHC class II invariant peptide, (CLIP). In most individuals, a control cell, known as a T regulatory cell (Treg for short), has been shown, to kill the activated B cell. If naïve B cell MHC molecules are engaged prior to B cell antigen receptor engagement, the consequence for the B cell is cell death (Newell, et al. PNAS 90 (3) 1127-1131, 1993). It has been shown that products of bacteria, viruses, and parasites cause cell surface expression of CLIP in the groove of MHC class II and, most likely, MHC class I, over time through cross presentation. Because CLIP is a highly conserved self-peptide, traditional CD4 T cells do not recognize CLIP directly in the groove of MHC class II, as CD4 cells that could have recognized the molecule would have been deleted in the thymus. It has been found that CLIP in the groove of MHC class II on a cell not only would not be recognized by a conventional CD4 or CD8 T cell, but also that CLIP provides protection from MHC Class II or MHC class I mediated cell death when MHC class I or class II are engaged by a variety of ligands. Modulation of CLIP on the cell surface has profound implications for the treatment of many diseases. It has been demonstrated experimentally herein that removal of CLIP from the groove of MHC class II can assist in the regulation of a number of biological properties. The invention in some aspects is a method for reducing blood pressure in a subject. In other aspects the invention is a method for treating a subject having preeclampsia by administering a CLIP inhibitor to the subject.

A CLIP inhibitor as used herein is any molecule that reduces the association of a CLIP molecule with MHC, for instance, by binding to the MHC and blocking the CLIP-MHC interaction or inhibiting the expression of CLIP. The CLIP inhibitor may function by displacing CLIP from the surface of a CLIP molecule expressing cell. A CLIP molecule expressing cell is a cell that has MHC class I or II on the surface and includes a CLIP molecule within that MHC. Such cells include, for example, epithelial cells, endothelial cells, and cells of the vascular endothelium.

The CLIP molecule, as used herein, refers to intact CD74 (also referred to as invariant chain) or intact CLIP, as well as the naturally occurring proteolytic fragments thereof. Intact CD74 or intact CLIP refer to peptides having the sequence of the native CD74 or native CLIP respectively. The CLIP molecule is one of the naturally occurring proteolytic fragments of CD74 or CLIP in some embodiments. The CLIP molecule may be, for example, at least 90% homologous to the native CD74 or CLIP molecules. In other embodiments the CLIP molecule may be at least 91%, 92%, 93%, 94%, 95%, 96%, 97%, 98%, or 99% homologous to the native CD74 or CLIP molecules An example of native CLIP molecule is MRMAT-PLLM (SEQ ID NO: 1), and in three-letter abbreviation as: Met Arg Met Ala Thr Pro Leu Leu Met (SEQ ID NO: 1). An example of native CD74 molecule is MHRRRSRSCR EDQKPVMDDQ RDLISNNEQL PMLGRRPGAP ESKCS-RGALY TGFSILVTLL AGQATTAYF LYQQQGRLDK LTVTSQNLQL ENLRMKLPKP PKPVSKMRMA TPLLMQALPM GALPQGPMQN ATKYGNMTED HVMHLLQNAD PLKVYPPLKG SFPENLRHLK NTMETIDWKV FESWMHHWLL FEMSRHSLEQ KPTDAPPKVL TKCQEEVSHI PAVHPGSFRP KCDENGNYLP LQCYGSIGYC WCVFPNGTEV PNTRSRGHHN CSESLELEDP SSGLGVTKQD LGPVPM (SEQ ID NO 88).

The function of the CLIP molecule in this invention is mainly as an MHC class I or MHC class II chaperone and protective shield. MHC class II molecules are heterodimeric complexes that present foreign antigenic peptides on the cell surface of antigen-presenting cells (APCs) to CD4+ T cells. MHC class II synthesis and assembly begins in the endoplasmic reticulum (ER) with the non-covalent association of the MHC α and β chains with trimers of CD74. CD74 is a non-polymorphic type II integral membrane protein; murine CD74 has a short (30 amino acid) N-terminal cytoplasmic tail, followed by a single 24 amino acid transmembrane region and an ~150 amino acid long lumenal domain. Three MHC class II αβ dimers bind sequentially to a trimer of the CD74 to form a nonameric complex (αβIi), which then exits the ER. After being transported to the trans-Golgi, the αβIi complex is diverted from the secretory pathway to the endocytic system and ultimately to acidic endosome or lysosome-like structures called MHC class I or II compartments.

The N-terminal cytoplasmic tail of CD74 contains two extensively characterized dileucine-based endosomal targeting motifs. These motifs mediate internalization from the plasma membrane and from the trans-Golgi network. In the endocytic compartments, the CD74 chain is gradually proteolytically processed, leaving only a small fragment, the class II-associated CD74 chain peptide (CLIP), bound to the released αβ dimers. The final step for MHC class II expression requires interaction of αβ-CLIP complexes with another class II-related αβ dimer, called HLA-DM in the human system. This drives out the residual CLIP, rendering the αβ dimers ultimately competent to bind antigenic peptides, which are mainly derived from internalized antigens and are also delivered to the endocytic pathway. The peptide-loaded class II molecules then leave this compartment by an unknown route to be expressed on the cell surface and surveyed by CD4+ T cells.

CLIP inhibitors include peptides and small molecules that can replace CLIP. In some embodiments the CLIP inhibitor is a peptide. A number of peptides useful for displacing CLIP molecules are described in U.S. patent application Ser. No. 12/508,543 (publication number US-2010-0166782-A1); Ser. No. 12/739,459 (publication number US-2011-0118175) and Ser. No. 12/508,532 (publication number US-2010-0166789-A1) each of which is herein specifically incorporated by reference. For instance a number of these peptides are "thymus nuclear protein (TNP)" peptides.

CLIP inhibitors include for instance but are not limited to competitive CLIP fragments, MHC class II binding peptides and peptide mimetics. Thus, the CLIP inhibitor includes peptides and peptide mimetics that bind to MHC class II and displace CLIP. For instance, an isolated peptide comprising $X_1RX_2X_3X_4X_5LX_6X_7$ (SEQ ID NO: 3), wherein each X is an amino acid, wherein R is Arginine, L is Leucine and wherein at least one of $X_2$ and $X_3$ is Methionine, wherein the peptide is not N-MRMATPLLM-C (SEQ ID NO: 1), and wherein the peptide is a CLIP displacer is provided according to the invention. X refers to any amino acid, naturally occurring or modified. In some embodiments the Xs referred to the in formula $X_1RX_2X_3X_4X_5LX_6X_7$ (SEQ ID NO: 8) have the following values:

$X_1$ is Ala, Phe, Met, Leu, Ile, Val, Pro, or Trp
$X_2$ is Ala, Phe, Met, Leu, Ile, Val, Pro, or Trp
$X_3$ is Ala, Phe, Met, Leu, Ile, Val, Pro, or Trp.
wherein $X_4$ is any
$X_5$ is Ala, Phe, Met, Leu, Ile, Val, Pro, or Trp
$X_6$ is any
$X_7$ is Ala, Cys, Thr, Ser, Gly, Asn, Gln, Tyr.

The peptide preferably is FRIM$X_4$VL$X_6$S (SEQ ID NO: 6), such that $X_4$ and $X_6$ are any amino acid and may be Ala. Such a peptide is referred to as FRIMAVLAS (SEQ ID NO: 5). Other preferred peptides of the invention include: IRIMATLAI (SEQ ID NO: 4), FRIMAVLAI (SEQ ID NO: 10), and IRIMAVLAS (SEQ ID NO: 11).

The minimal peptide length for binding HLA-DR is 9 amino acids. However, there can be overhanging amino acids on either side of the open binding groove. For some well-studied peptides, it is known that additional overhanging amino acids on both the N and C termini can augment binding. Thus the peptide may be 9 amino acids in length or it may be longer. For instance, the peptide may have additional amino acids at the N and/or C terminus. The amino acids at either terminus may be anywhere between 1 and 100 amino acids. In some embodiments the peptide includes 1-50, 1-20, 1-15, 1-10, 1-5 or any integer range there between. When the peptide is referred to as "N-FRIMAVLAS-C" (SEQ ID NO: 7) or "N-$X_1RX_2X_3X_4X_5LX_6X_7$-C" (SEQ ID NO: 9) the —C and —N refer to the terminus of the peptide and thus the peptide is only 9 amino acids in length. However the 9 amino acid peptide may be linked to other non-peptide moieties at either the —C or —N terminus or internally.

Other peptides useful as CLIP inhibitors, including some TNP peptides and synthetic peptides are shown in Table 1.

TABLE 1

| Amino Acid Sequence | SEQ ID NO. |
|---|---|
| LVQNDTLLQ | 12 |
| VVSTQTALA | 13 |
| IMNSFVNDI | 14 |
| MGIMKSFVN | 15 |
| MGIMNSFVN | 16 |
| VLIAFSQYL | 17 |
| IMNSFVNDL | 18 |
| IMKSFVNDI | 19 |
| IQGITKPAI | 20 |
| VTAMDVVYA | 21 |
| YGFQNALIV | 22 |
| LVNELTEFA | 23 |
| FQNALIVRY | 24 |
| MSIMNSFVN | 25 |
| LVLIAFSQY | 26 |
| VQNDTLLQV | 27 |

TABLE 1-continued

| Amino Acid Sequence | SEQ ID NO. |
|---|---|
| MGNMNSFVN | 28 |
| FQSAIKLVD | 29 |
| VAFVDKCCA | 30 |
| LVVSTQTAL | 31 |
| VFLENVIRD | 32 |
| LIAFSQYLQ | 33 |
| FQSAAIGAL | 34 |
| MDIMNSFVN | 35 |
| IKLVDFQDA | 36 |
| VMENFVAFV | 37 |
| YLQQCPFDE | 38 |
| VLPNIQAVL | 39 |
| VEPSDTIEN | 40 |
| FFQSAIKLV | 41 |
| IQAVLLPKK | 42 |
| IAFSQYLQQ | 43 |
| FLGSFLYEY | 44 |
| FVNDIFERI | 45 |
| LPNIQAVLL | 46 |
| LLPGELAKH | 47 |
| FVAFVDKCC | 48 |
| LKPDPNTLC | 49 |
| MENFVAFVD | 50 |
| LFGDELCKV | 51 |
| VTIAQGGVL | 52 |
| MKSFVNDIF | 53 |
| LFTFHADIC | 54 |
| FVNDLFERL | 55 |
| IAQGGVLPN | 56 |
| LGSFLYEYS | 57 |
| FVDKCCAAD | 58 |
| LFEDTNLCA | 59 |
| VNFAEFSKK | 60 |
| MNSFVNDIF | 61 |
| MNSFVNDLF | 62 |
| LVDEPQNLI | 63 |
| MDVVYALKR | 64 |
| LLLPGELAK | 65 |

TABLE 1-continued

| Amino Acid Sequence | SEQ ID NO. |
|---|---|
| LTPDETYVP | 66 |
| LQNEIDVSS | 67 |
| LVDFQDAKA | 68 |
| VGLFEDTNL | 69 |
| LGLIYEETR | 70 |
| ILGLIYEET | 71 |
| IDVSSREKS | 72 |
| LHTLFGDEL | 73 |
| LVGLFEDTN | 74 |
| IAQDFKTDL | 75 |
| FHADICTLP | 76 |

In some instances the peptides may be mixed with cystatin A and/or histones and in other instances the composition is free of cystatin A or histones. Histone encompasses all histone proteins including HI, H2A, $H_2B$, H3, H4 and H5.

The peptide may be cyclic or non-cyclic. Cyclic peptides in some instances have improved stability properties. Those of skill in the art know how to produce cyclic peptides.

The peptides may also be linked to other molecules. The two or more molecules may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

The peptide for instance, may be linked to a PEG or TEG molecule. Such a molecule is referred to as a PEGylated or TEGylated peptide.

In certain embodiments, the CLIP inhibitor is an inhibitory nucleic acid such as a small interfering nucleic acid molecule such as antisense, RNAi, or siRNA oligonucleotide to reduce the level of mature CLIP molecule (CD74) expression. The nucleotide sequences of CD74 molecules are well known in the art and can be used by one of skill in the art using art recognized techniques in combination with the guidance set forth herein to produce the appropriate siRNA molecules. An example of a CD74 nucleic acid molecule is shown in SEQ ID NO. 77:

```
ccgggggtc agggtcccag atgcacagga ggagaagcag gagctgtcgg gaagatcaga agccagtcat ggatgaccag cgcgacctta tctccaacaa tgagcaactg cccatgctgg gccggcgccc tggggccccg gagagcaagt gcagccgcgg
```

```
agccctgtac acaggctttt ccatcctggt gactctgctc ctcgctggcc aggccaccac cgcctacttc ctgtaccagc agcagggccg gctggacaaa ctgacagtca cctcccagaa cctgcagctg gagaacctgc gcatgaagct tcccaagcct cccaagcctg tgagcaagat gcgcatggcc accccgctgc tgatgcaggc gctgcccatg ggagccctgc cccaggggcc catgcagaat gccaccaagt atggcaacat gacagaggac catgtgatgc acctgctcca gagtcactgg aactggagga cccgtcttct gggctgggtg tgaccaagca ggatctgggc ccagtcccca tgtgagagca gcagaggcgg tcttcaacat cctgccagcc ccacacagct acagctttct tgctcccttc agcccccagc ccctccccca tctcccaccc tgtacctcat cccatgagac cctggtgcct ggctctttcg tcacccttgg acaagacaaa ccaagtcgga acagcagata acaatgcagc aaggccctgc tgcccaatct ccatctgtca acagggcgt gaggtcccag gaagtggcca aaagctagac agatcccgt tcctgacatc acagcagcct ccaacacaag gctccaagac ctaggctcat ggacgagatg ggaaggcaca gggagaaggg ataaccctac acccagaccc caggctggac atgctgactg tcctctcccc tccagcctt ggccttggct tttctagcct atttacctgc aggctgagcc actctcttcc ctttccccag catcactccc caaggaagag ccaatgtttt ccaccataa tcctttctgc cgaccctag ttccctctgc tcagccaagc ttgttatcag ctttcagggc catggttcac attagaataa aaggtagtaa ttagaacaaa aaaaaaaaa aaaaa
```

Small interfering nucleic acid (siNA) include, for example: microRNA (miRNA), small interfering RNA (siRNA), double-stranded RNA (dsRNA), and short hairpin RNA (shRNA) molecules. An siNA useful in the invention can be unmodified or chemically-modified. An siNA of the instant invention can be chemically synthesized, expressed from a vector or enzymatically synthesized. Such methods are well known in the art. Exemplary single stranded regions of siRNA for CLIP are shown below. The invention contemplates others as well.

```
                              (SEQ ID NO. 78)
GGUAGUAAUUAGAACAAAA (SEQ ID NO. 79)
GGUUCACAUUAGAAUAAAA (SEQ ID NO. 80)
GAACAAAAAAAAAAAAAA (SEQ ID NO. 81)
CAAAAAAAAAAAAAAAAAA (SEQ ID NO. 82)
AGAACAAAAAAAAAAAAAA (SEQ ID NO. 83)
ACAAAAAAAAAAAAAAAAA (SEQ ID NO. 84)
GUAAUUAGAACAAAAAAA (SEQ ID NO. 85)
CAUGGUUCACAUUAGAAUA (SEQ ID NO. 86)
GUAGUAAUUAGAACAAAA (SEQ ID NO. 87)
GGCUUUUCUAGCCUAUUUA
```

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

Other inhibitor molecules that can be used include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat. Med. 4(8):967-71, 1998). For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):

643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

The invention involves methods for treating a subject. A subject shall mean a human or vertebrate mammal including but not limited to a dog, cat, horse, goat and primate, e.g., monkey. Thus, the invention can also be used to treat diseases or conditions in non-human subjects. Preferably the subject is a human. In some embodiments the subject has Preeclampsia. Preeclampsia is a disorder typically observed in women who are at least 20 weeks pregnant that is associated with the development of hypertension and proteinuria, generally in the form of albuminuria, and the supervention of excessive edema.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

When used in combination with the therapies of the invention the dosages of known therapies may be reduced in some instances, to avoid side effects.

The CLIP inhibitor can be administered in combination with other therapeutic agents and such administration may be simultaneous or sequential. When the other therapeutic agents are administered simultaneously they can be administered in the same or separate formulations, but are administered at the same time. The administration of the other therapeutic agent and the CLIP inhibitor can also be temporally separated, meaning that the therapeutic agents are administered at a different time, either before or after, the administration of the CLIP inhibitor. The separation in time between the administration of these compounds may be a matter of minutes or it may be longer.

The active agents of the invention are administered to the subject in an effective amount for treating disorders such as preeclampsia. An "effective amount", for instance, is an amount necessary or sufficient to realize a desired biologic effect. An effective amount for treating preeclampsia may be an amount sufficient to decrease blood pressure levels as compared to blood pressure levels obtained before treatment or as compared to control normal blood pressure levels. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, a sub-therapeutic dosage of either or both of the molecules may be used. A "sub-therapeutic dose" as used herein refers to a dosage which is less than that dosage which would produce a therapeutic result in the subject if administered in the absence of the other agent.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards. The compounds are generally suitable for administration to humans. This term requires that a compound or composition be non-toxic and sufficiently pure so that no further manipulation of the compound or composition is needed prior to administration to humans.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

In any case, the composition may comprise various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bio-erodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Therapeutic formulations of the peptides or antibodies may be prepared for storage by mixing a peptide or antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The peptide may be administered directly to a cell or a subject, such as a human subject alone or with a suitable carrier. Alternatively, a peptide may be delivered to a cell in vitro or in vivo by delivering a nucleic acid that expresses the peptide to a cell. Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half-life, and the like. Polymeric delivery systems also have been used successfully to deliver nucleic acid molecules into cells, as is known by those skilled in the art. Such systems even permit oral delivery of nucleic acid molecules.

The peptide of the invention may also be expressed directly in mammalian cells using a mammalian expression vector. Such a vector can be delivered to the cell or subject and the peptide expressed within the cell or subject. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the α-fetoprotein promoter.

As used herein, a "vector" may be any of a number of nucleic acid molecules into which a desired sequence may be inserted by restriction and ligation for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript.

The invention also includes articles, which refers to any one or collection of components. In some embodiments the articles are kits. The articles include pharmaceutical or diagnostic grade compounds of the invention in one or more containers. The article may include instructions or labels promoting or describing the use of the compounds of the invention.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of preeclampsia or other diseases associated with aberrant blood pressure.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Effects of TLR Agonists with or without a CLIP Inhibitor on Blood Pressure in Pregnant Mice In order to determine whether the displacement of CLIP with a peptide in the absence or presence of a TLR ligand resulted in changes in blood pressure in pregnant mice the following experiment was performed.

Methods

Experimental Design: C57BL/6 female mice were bred with male C57BL/6 mice. At day 13 mice were injected IP with vehicle, Poly I:C (SIGMA PO913 50 mg), CLO097 (Invivogen tlrl-C95-5), or R837 (Invivogen tlrl imq) with or without TPP (FRIMAVLAS (SEQ ID NO: 5). Mice were injected a total of 3 times, every other day. At day 18 mice were euthanized, uterus/pups, blood, blood vessels, and spleen were removed.

Blood Pressure: Systolic arterial blood pressure was measured by tail-cuff plethysmography. Rats were trained for three days prior to data collection. Animals were warmed to 32° C. and measurements were taken using an IITC Model 59 amplifier (Woodland Hills, Calif.), a system which correlates well with telemetry measurements of systolic blood pressure.

Results:

Pregnant mice (P) were treated with one of three TLR agonists to induce a physiological condition which mimics preeclampsia. Poly I:C is a TLR3 agonist and is well established in inducing characteristics of preeclampsia in mice. R837 is a single stranded RNA activator of TLR7 but not TLR8. Similar to Poly I:C R837 induces characteristics of preeclampsia in mice. CLO097 is a single stranded RNA that activates TLR7 and TLR8. While CLO097 induces some of the characteristics of preeclampsia the response is somewhat muted. Half of the mice were also treated with TPP in order to displace CLIP. Control pregnant mice received vehicle or vehicle plus TPP. The blood pressure of each mouse was measured on day 17 following treatment. The data is shown in FIG. 1. Normal pregnant mice (P) maintained a constant blood pressure when treated with vehicle and TPP, suggesting that TPP does not have an effect on the blood pressure under normal conditions. The three groups of mice treated with R837, CLO097 or Poly I:C (PIC) experienced significantly increased blood pressure. The mice that were treated with a TLR agonist and a TPP peptide, however, exhibited normal blood pressure, demonstrating that peptide treatment was sufficient to dramatically reduce blood pressure induced by the TLR agonists.

Figure 2A:
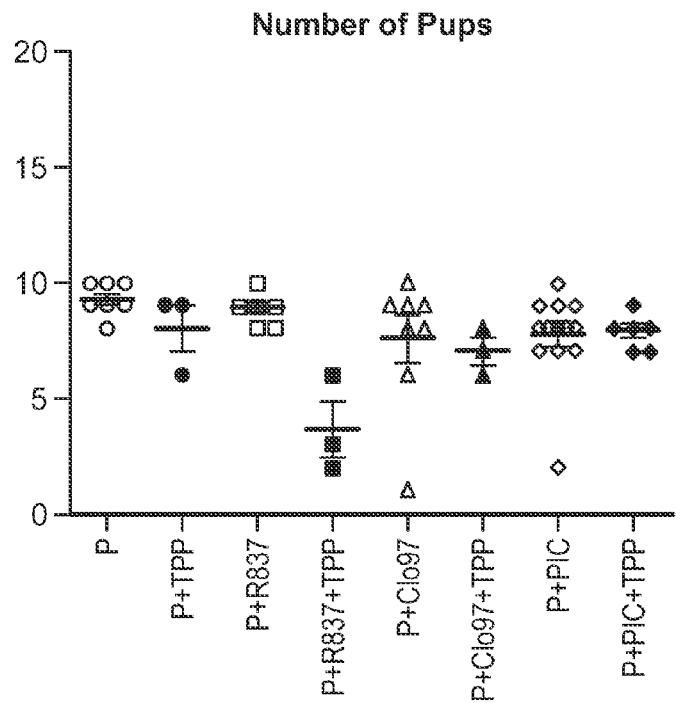
FIGS. 2A and 2B are a set of graphs depicting the effects of the treatment conditions described in FIG. 1 on the total number of pups (2A) and the number of malformed pups (2B) that were present at day 18 following treatment.
Figure 2B:
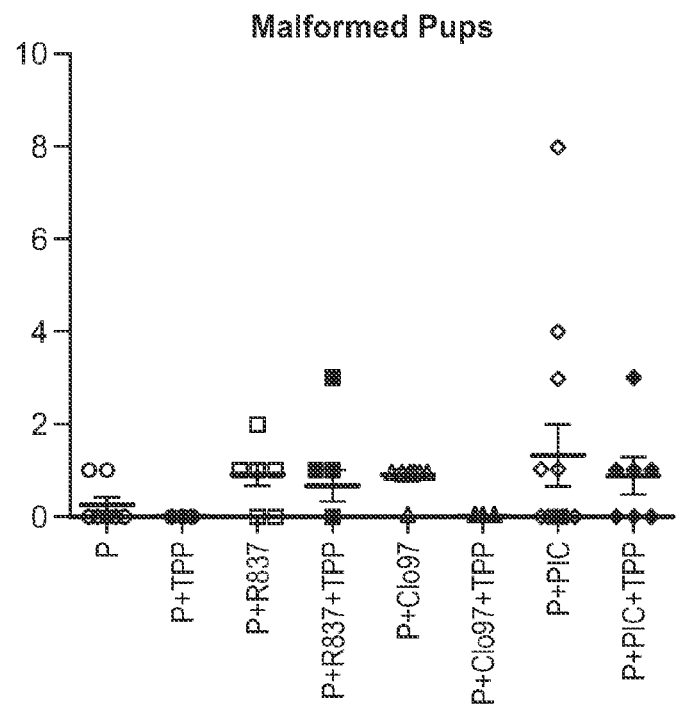

FIG. 2 shows the effects of the treatment conditions on the total number of pups (2A) and the number of malformed pups (2B) that were present at day 18 following treatment. The number of pups and malformed pups was relatively consistent across all groups at this time point. These data suggest that the peptide caused no increase in the number of malformations or number of pups with respect to normal pregnancies or pregnancies treated with TLR agonists.

Example 2

Effects of TLR Agonists with or without a CLIP Inhibitor on Relaxation Markers in Pregnant Mice Having Stimulated Contractions In order to determine whether the displacement of CLIP with peptide in the absence or presence of a TLR ligand resulted in changes in contractions during pregnancy the following experiment was performed.

Methods

Experimental Design: Mice were treated as described in Example 1.

Vasodilation/Endothelial Function: Aortic rings were connected to an isometric force transducer in a custom-made 15-ml organ chamber filled with 37° C. physiological salt solution (119 mM NaCl, 4.7 mM KCl, 25 mM NaHCO3, 1.18 mM KH2PO4, 1.17 mM MgSO4-7H2O, 11.1 mM Dextrose, 2.5 mM $CaCl_2$) with 95% $O_2$-5% CO2. All experiments were performed in the presence of indomethacin (10 mM) to inhibit prostacyclin production by cyclooxygenase. Passive tension on the vessels was set at 400 mg based on previously generated length-tension curves, and isometric force generation was recorded continuously with a PowerLab system (AD Instruments, Colorado Springs, Colo.). After a 60-min equilibration period, vessels were contracted with phenylephrine (0.1-1 mM) and repeated until reproducible contractions were obtained. Acetylcholine (10 mM) was administered to test the functional integrity of endothelium as measured by a relaxation response. Concentration-response curves were obtained in a half-log, cumulative fashion in response to acetylcholine (1 nM to 100 mM) following contraction to an EC70 concentration of phenylephrine. Relaxation responses were expressed as percent relaxation from phenylephrine-induced contraction.

Figure 3A:
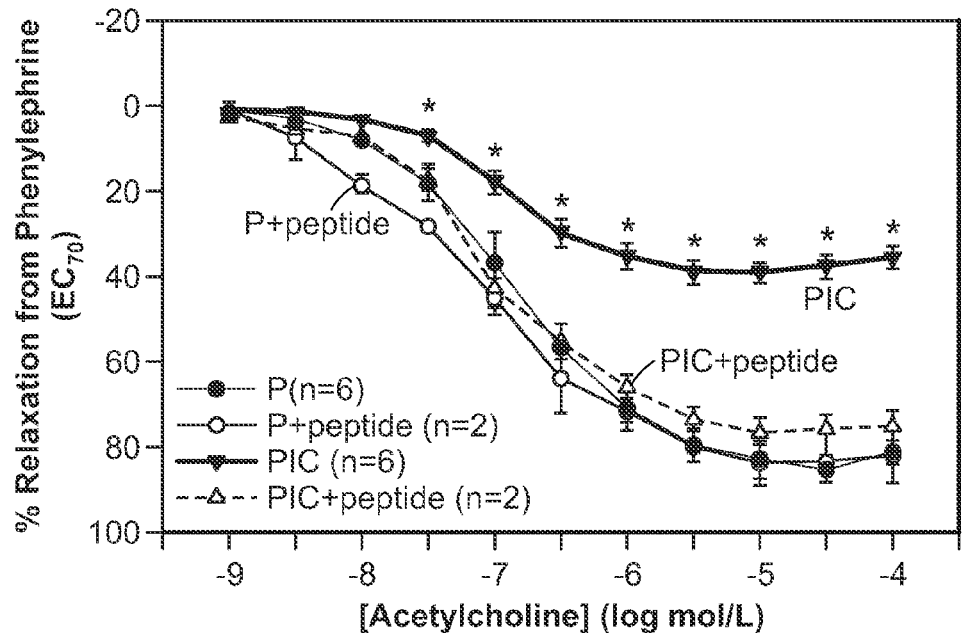
FIGS. 3A and 3B are a set of graphs depicting the effects of poly I:C (PIC) with or without TPP (peptide of SEQ ID NO: 5) on relaxation markers in pregnant mice having phenylephrine stimulated contractions. The blood vessels were treated with acetylcholine (3A) or sodium nitroprusside(3B) to induce a relaxation response.
Figure 3B:
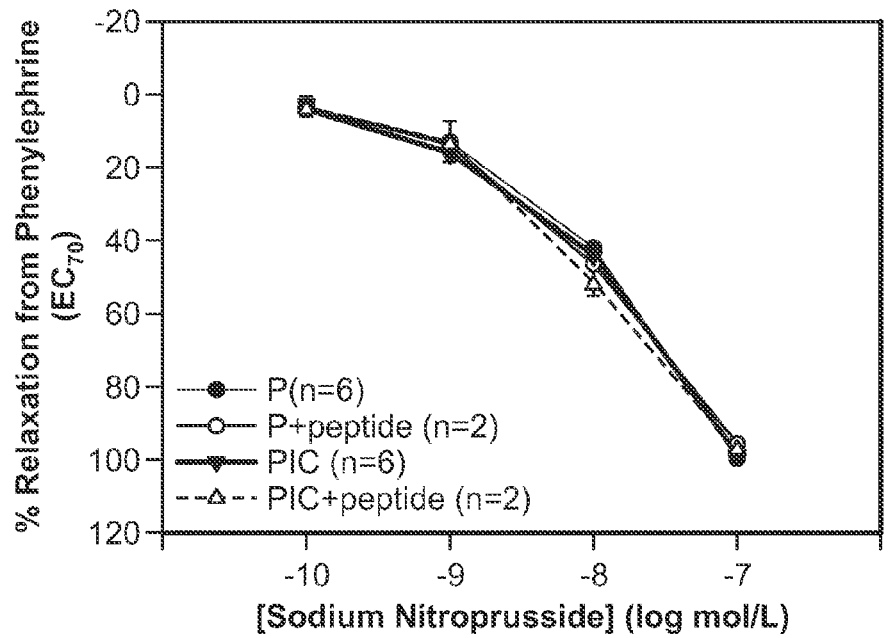
Figure 4A:
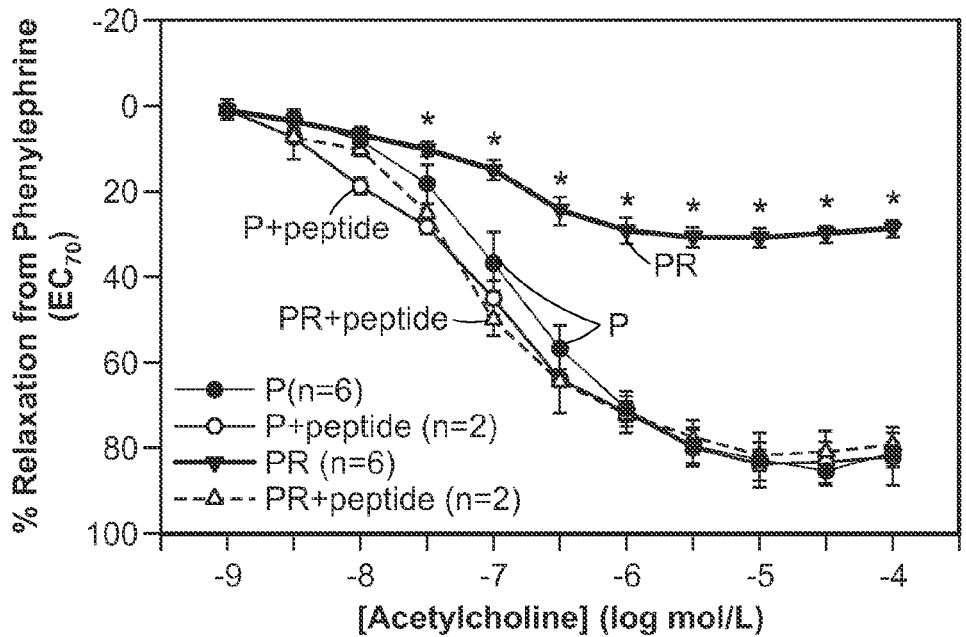
FIGS. 4A and 4B are a set of graphs depicting the effects of R837 (PR) with or without TPP (peptide of SEQ ID NO: 5) on relaxation markers in pregnant mice having phenylephrine stimulated contractions. The blood vessels were treated with acetylcholine (4A) or sodium nitroprusside (4B) to induce a relaxation response.
Figure 4B:
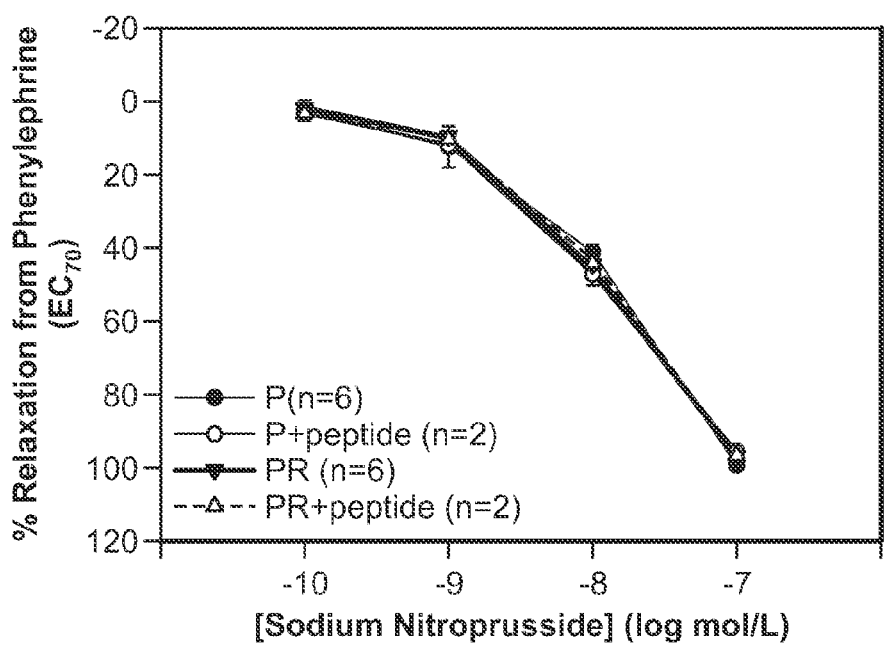
Figure 5A:
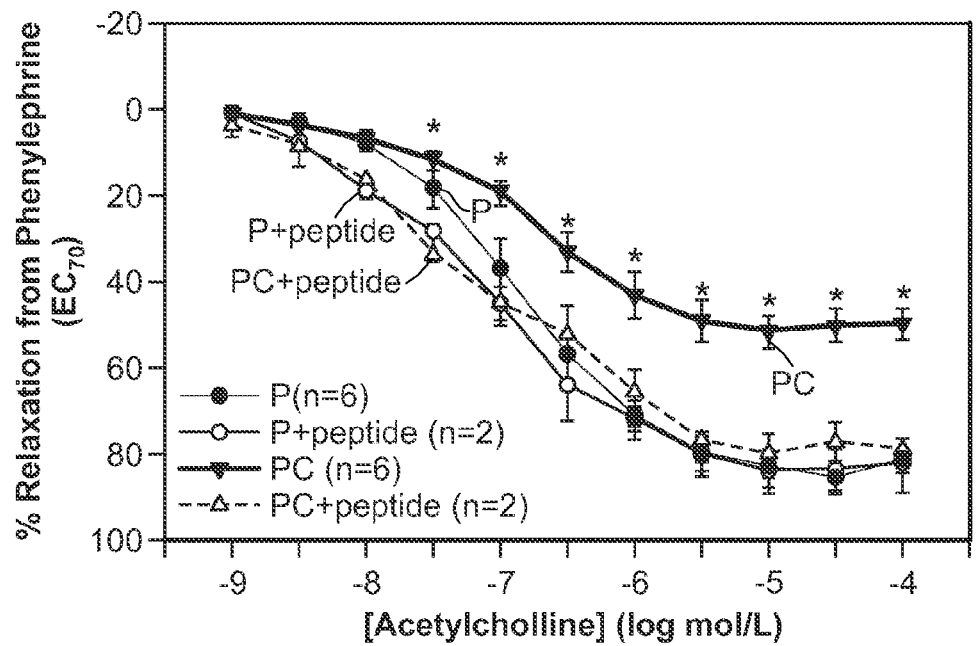
FIGS. 5A and 5B are a set of graphs depicting the effects of CLO097 (PC) with or without TPP (peptide of SEQ ID NO: 5) on relaxation markers in pregnant mice having phenylephrine stimulated contractions. The blood vessels were treated with acetylcholine (5A) or sodium nitroprusside (5B) to induce a relaxation response.
Figure 5B:
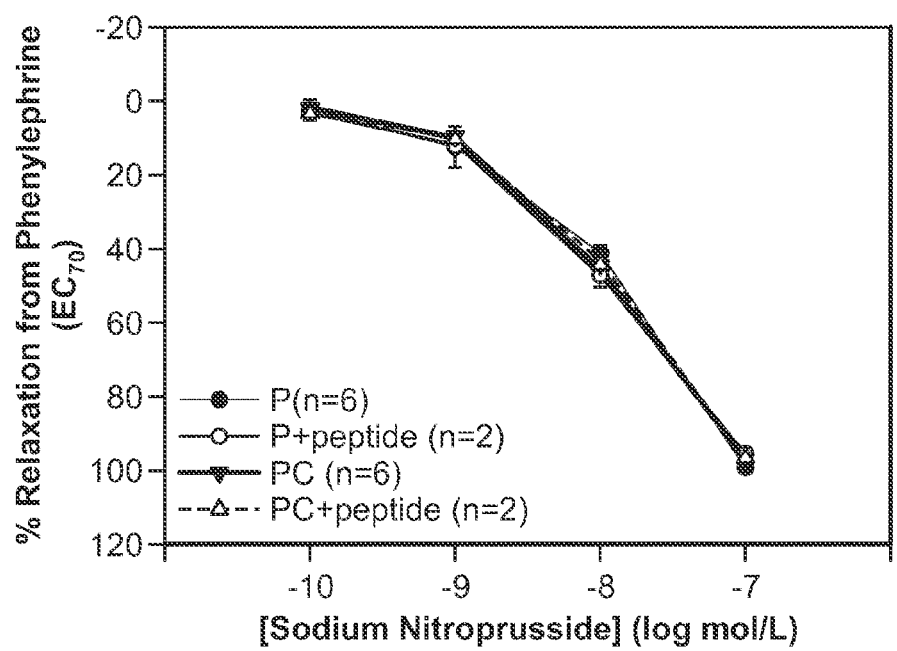

Results:

In order to examine the effects of TLR agonist and/or CLIP inhibitor treatment on vasodilation/endothelium function, blood vessels were isolated and examined using an isometric force transducer. The blood vessels were treated with phenylephrine to induce contractions and then with acetylcholine to induce a relaxation response. Control samples utilized sodium nitroprusside to induce relaxation. Treatment with sodium nitroprusside establish that the peptide effects were on endothelial cells, not on smooth muscle cells. The data is presented in FIG. 3 (poly I:C (PIC)+/−TPP (peptide); 3A acetylcholine, 3B sodium nitroprusside), FIG. 4 (R837 (PR)+/−TPP (peptide); 4A acetylcholine, 4B sodium nitroprusside), and FIG. 5 (Clo097 (PC)+/−TPP (peptide); 5A acetylcholine, 5B sodium nitroprusside). Under each of the three experimental conditions the relaxation response is delayed and TPP is able to restore the relaxation response to normal levels.

Example 3

Effects of TLR Agonists with or without a CLIP Inhibitor on Immune Cell Markers in Pregnant Mice In order to determine whether the displacement of CLIP with peptide in the absence or presence of a TLR ligand resulted in changes in immune cell markers the following experiment was performed.

Methods

Experimental Design: Mice were treated as described in Example 1. Splenocytes were isolated and stained for CD3, CD4, CD8, CD11b, Ly6G/C, CD25, FoxP3, CD19, B220, CD5, CLIP, and Gamma Delta TCR.

Figure 6A:
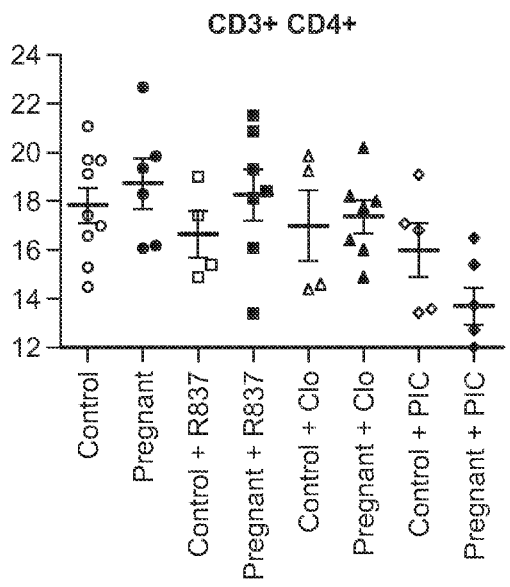
FIGS. 6A and 6B are a set of graphs showing the changes in expression of CD3 and CD4 on splenocytes of control or pregnant (P) mice treated with R837, CLO097 (Clo) or poly I:C (PIC) but without TPP (6A) and pregnant mice treated with TPP, R837 and/or TPP, CLO097 (Clo) and/or TPP or poly I:C (PIC) and/or TPP (6B, the two graphs depict the results of two separate experiments).
Figure 6B:
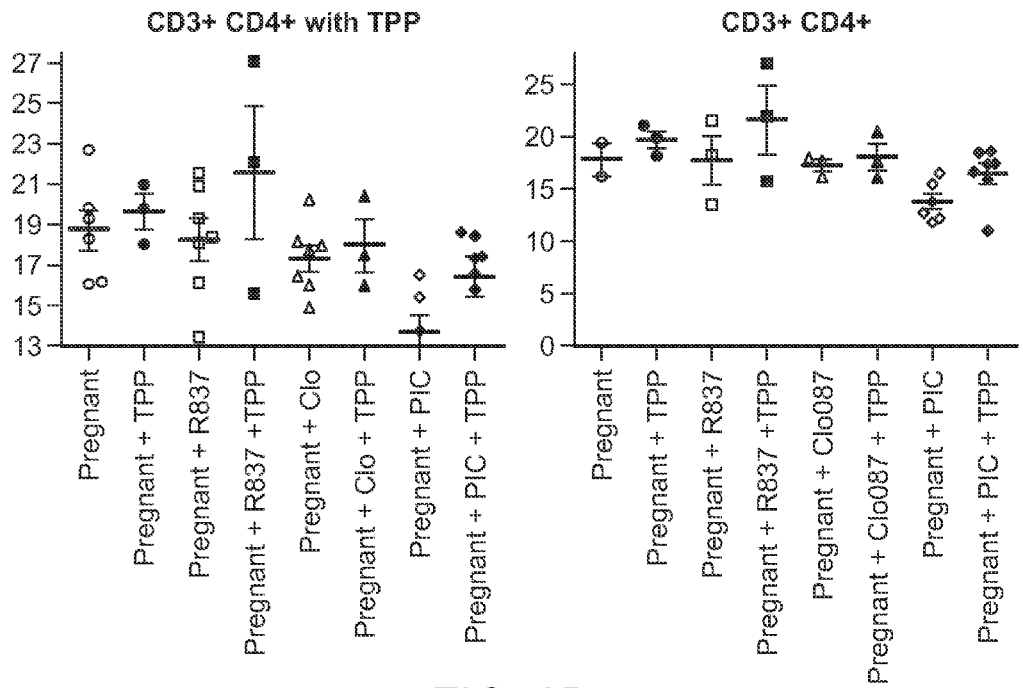

Results:

The results of the immune cell marker analysis are shown in FIGS. 6-9. FIG. 6 is a set of graphs showing the changes in expression of CD3 and CD4 on splenocytes. FIG. 6A examines CD3 and CD4 levels on control or pregnant (P) mice treated with R837, CLO097 (Clo) or poly I:C (PIC) but without TPP. Pregnant mice treated with TPP, R837 and/or TPP, CLO097 (Clo) and/or TPP or poly I:C (PIC) and/or TPP were used to examine CD3 and CD4 splenocyte levels and the data is shown in FIG. 6B (the two graphs depict the results of two separate experiments).

Figure 7A:
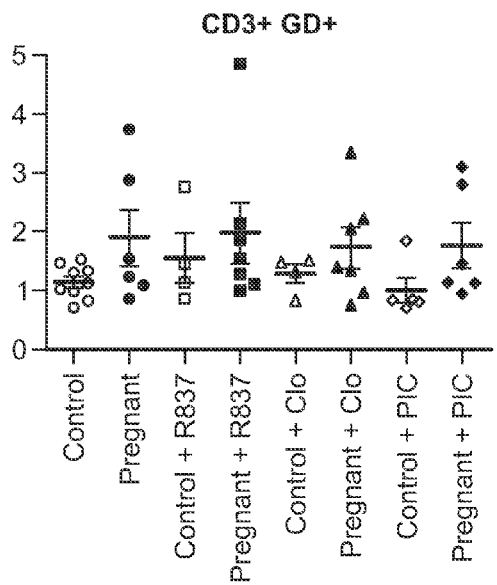
FIGS. 7A and 7B are a set of graphs showing the changes in expression of CD3 and gamma delta T-cells (GD) on splenocytes of control or pregnant (P) mice treated with R837, CLO097 (Clo) or poly I:C (PIC) but without TPP (7A) and pregnant mice treated with TPP, R837 and/or TPP, CLO097 (Clo) and/or TPP or poly I:C (PIC) and/or TPP (7B, the two graphs depict the results of two separate experiments).
Figure 7B:
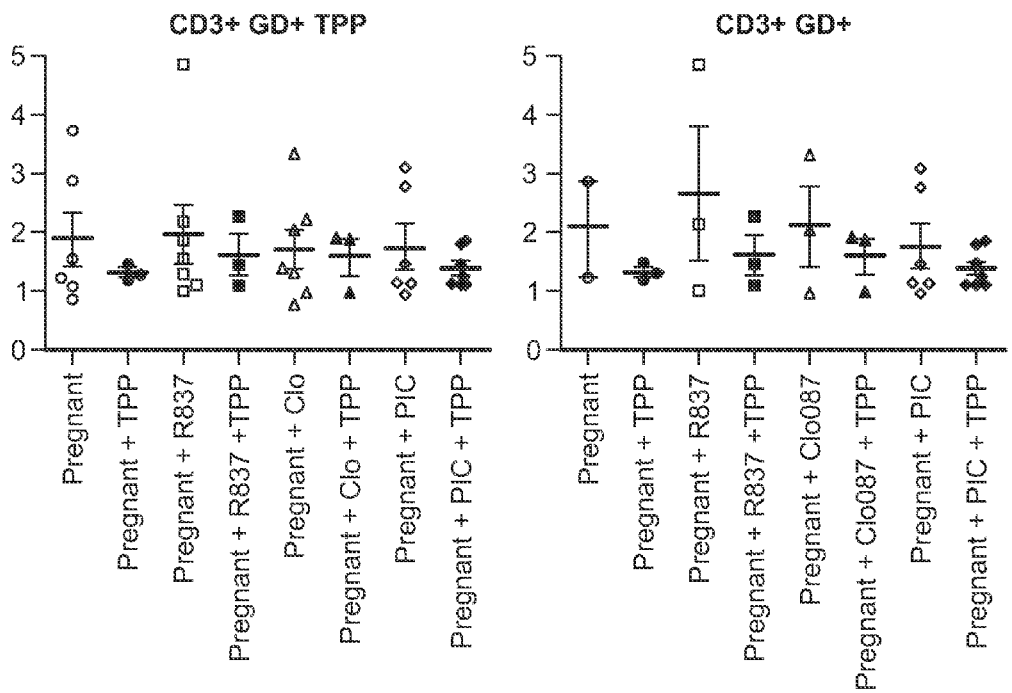

FIG. 7 is a set of graphs showing the changes in expression of CD3 and gamma delta T-cells (GD) on splenocytes. FIG. 7A examines CD3 and GD levels on control or pregnant (P) mice treated with R837, CLO097 (Clo) or poly I:C (PIC) but without TPP. Pregnant mice treated with TPP, R837 and/or TPP, CLO097 (Clo) and/or TPP or poly I:C (PIC) and/or TPP were used to examine CD3 and GD splenocyte levels and the data is shown in FIG. 7B (the two graphs depict the results of two separate experiments).

Figure 8A:
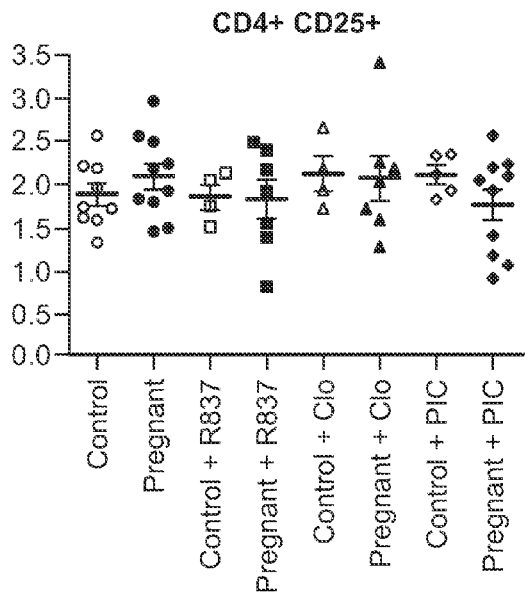
FIGS. 8A and 8B are a set of graphs showing the changes in expression of CD4 and CD25 on splenocytes.
Figure 8B:
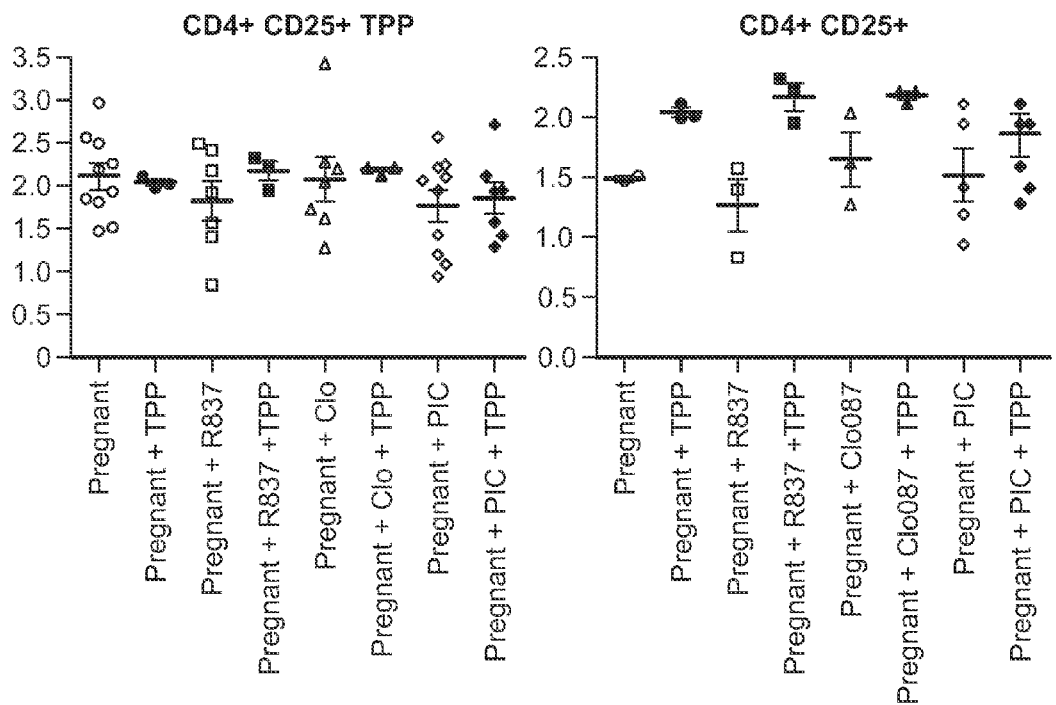

FIG. 8 is a set of graphs showing the changes in expression of CD4 and CD25 on splenocytes. FIG. 8A examines CD3 and CD25 levels on control or pregnant (P) mice treated with R837, CLO097 (Clo) or poly I:C (PIC) but without TPP. FIG. 8B examines CD3 and CD25 levels on pregnant (P) mice treated with TPP, R837 and/or TPP, CLO097 (Clo) and/or TPP or poly I:C (PIC) and/or TPP (the two graphs depict the results of two separate experiments).

Figure 9A:
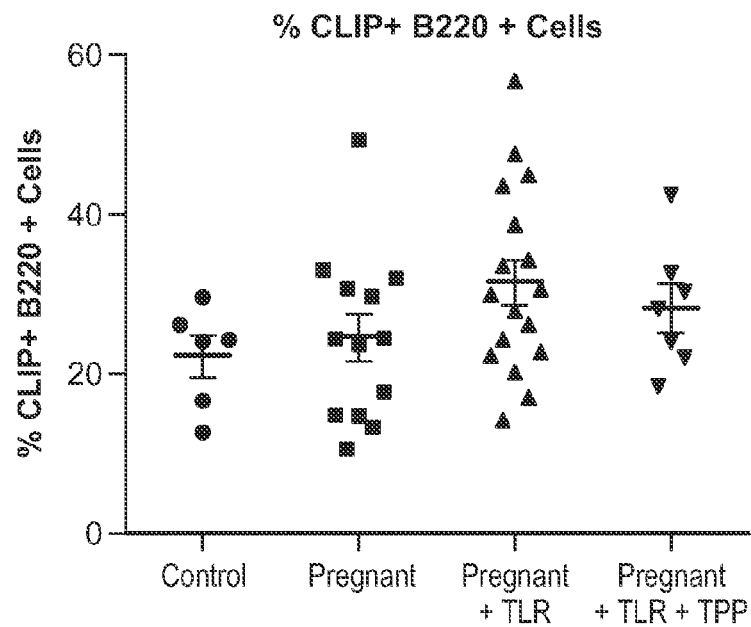
FIGS. 9A-9C are a set of graphs which depicts the removal of all CLIP (9A) versus bright CLIP (9B) from the surface of B220 cells. TPP is effective in removing bright CLIP with respect to TLR induced levels.
Figure 9B:
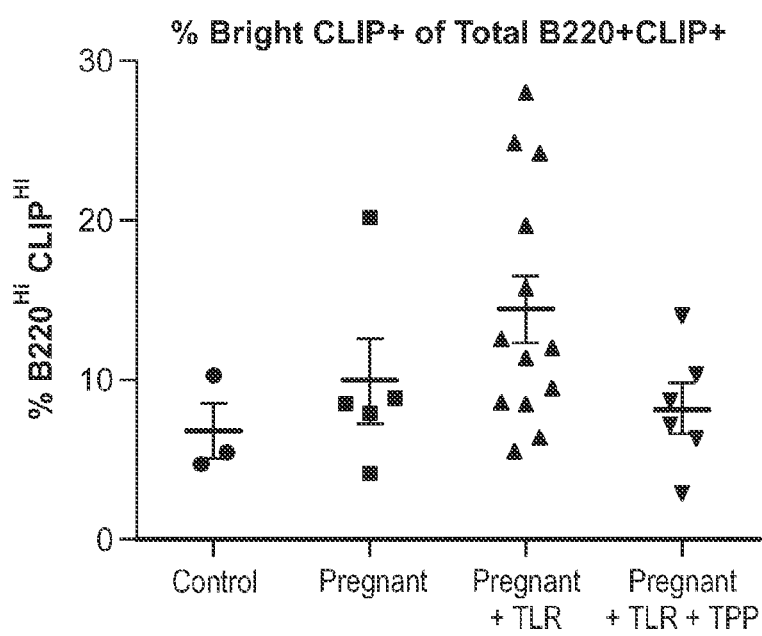
Figure 9C:
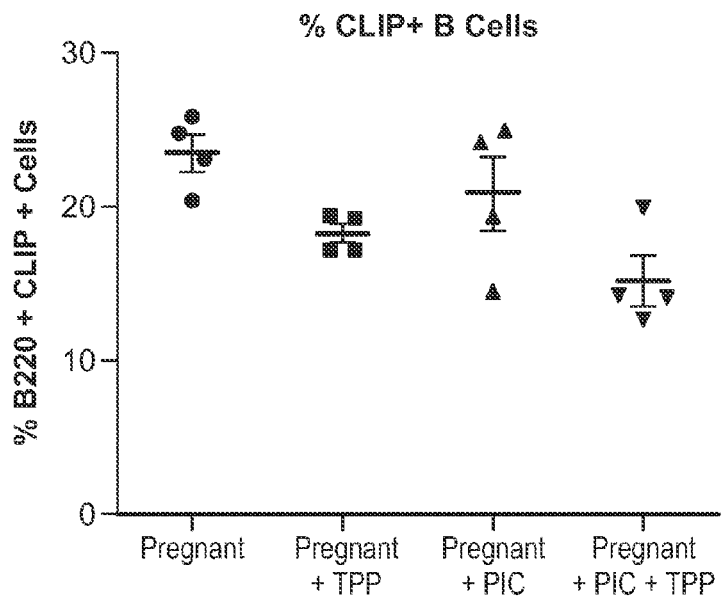
Figure 10:
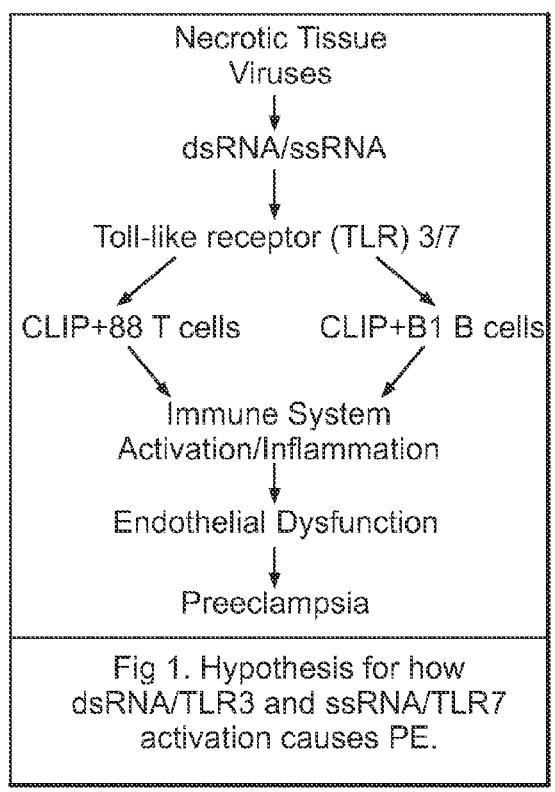
FIG. 10 is a flowchart which depicts the proposed mechanism for how dsRNA/TLR3 and ssRNA/TLR7 activation causes PE.

FIG. 9 is a set of graphs that depicts the removal of all CLIP (9A) versus bright CLIP (9B) and FIG. 9C from the surface of B220 cells. TPP is effective in removing bright CLIP with respect to TLR induced levels. TLR agonists include CLO097; R837, and Poly I:C. FIG. 9C depicts the percentage of CLIP+cells resulting from Poly I:C stimulation with and without TPP.

Example 4

Analysis of Allele Frequencies for Identifying CLIP Inhibitory Peptides

A weighted prediction program was used to analyze a series of allele frequencies from the following 4 populations.
1. Allele frequency of the total Colorado population (ie. the weighted average of all Colorado ethnicities: Caucasian, Hispanic, African American, Asian).
2. Allele frequency of the Caucasian Colorado population.
3. Allele frequency of the African American Colorado population
4. Allele frequency of the HLA-DR data available from South Africa, a 141 individual study from Limpopo Venda population The data for each of studies 1-4 is presented below in Tables 2-5. Briefly, the best peptides for each of the 4 studies is presented below
1. The best peptide for the allele frequency of the total Colorado population is IRIMATLAI (SEQ ID NO. 4).
2. The best peptide for the allele frequency of the Caucasian Colorado population is IRIMATLAI (SEQ ID NO. 4).
3. The best peptide for the allele frequency of the African American Colorado population is FRIMAVLAI (SEQ ID NO. 10).
4. The best peptide for the allele frequency of the HLA-DR data available from South Africa, a 141 individual study from Limpopo Venda population is IRIMAVLAS (SEQ ID NO. 11).

TABLE 2

Table 2: Allele Weighting (allele followed by weight is provided for each Study)

| Study 1 | Study 2 | Study 3 | Study 4 |
|---|---|---|---|
| HLA_DRB1-0101 0.0704 | HLA_DRB1-0101 0.085 | HLA_DRB1-0101 0.021 | HLA_DRB1-0101 0.103 |
| HLA_DRB1-0102 0.0197 | HLA_DRB1-0102 0.014 | HLA_DRB1-0102 0.033 | HLA_DRB1-0102 0.0 |
| HLA_DRB1-0301 0.106 | HLA_DRB1-0301 0.121 | HLA_DRB1-0301 0.002 | HLA_DRB1-0301 0.137 |
| HLA_DRB1-0305 0.0 | HLA_DRB1-0305 0.0 | HLA_DRB1-0305 0.0 | HLA_DRB1-0305 0.0 |
| HLA_DRB1-0306 0.0 | HLA_DRB1-0306 0.0 | HLA_DRB1-0306 0.0 | HLA_DRB1-0306 0.0 |
| HLA_DRB1-0307 0.0002 | HLA_DRB1-0307 0.0 | HLA_DRB1-0307 0.0 | HLA_DRB1-0307 0.0 |
| HLA_DRB1-0308 0.0 | HLA_DRB1-0308 0.0 | HLA_DRB1-0308 0.0 | HLA_DRB1-0308 0.0 |
| HLA_DRB1-0309 0.0 | HLA_DRB1-0309 0.0 | HLA_DRB1-0309 0.0 | HLA_DRB1-0309 0.0 |
| HLA_DRB1-0311 0.0 | HLA_DRB1-0311 0.0 | HLA_DRB1-0311 0.0 | HLA_DRB1-0311 0.0 |
| HLA_DRB1-0401 0.0678 | HLA_DRB1-0401 0.086 | HLA_DRB1-0401 0.025 | HLA_DRB1-0401 0.064 |
| HLA_DRB1-0402 0.0114 | HLA_DRB1-0402 0.011 | HLA_DRB1-0402 0.004 | HLA_DRB1-0402 0.0 |
| HLA_DRB1-0404 0.0403 | HLA_DRB1-0404 0.039 | HLA_DRB1-0404 0.012 | HLA_DRB1-0404 0.0 |
| HLA_DRB1-0405 0.0098 | HLA_DRB1-0405 0.007 | HLA_DRB1-0405 0.012 | HLA_DRB1-0405 0.0 |
| HLA_DRB1-0408 0.00517 | HLA_DRB1-0408 0.006 | HLA_DRB1-0408 0.006 | HLA_DRB1-0408 0.0 |
| HLA_DRB1-0410 0.0011 | HLA_DRB1-0410 0.0 | HLA_DRB1-0410 0.002 | HLA_DRB1-0410 0.0 |
| HLA_DRB1-0421 0.0 | HLA_DRB1-0421 0.0 | HLA_DRB1-0421 0.0 | HLA_DRB1-0421 0.0 |
| HLA_DRB1-0423 0.0 | HLA_DRB1-0423 0.0 | HLA_DRB1-0423 0.0 | HLA_DRB1-0423 0.0 |
| HLA_DRB1-0426 0.0 | HLA_DRB1-0426 0.0 | HLA_DRB1-0426 0.0 | HLA_DRB1-0426 0.0 |
| HLA_DRB1-0701 0.121 | HLA_DRB1-0701 0.132 | HLA_DRB1-0701 0.086 | HLA_DRB1-0701 0.056 |

TABLE 2-continued

Table 2: Allele Weighting (allele followed by weight is provided for each Study)

| Study 1 | Study 2 | Study 3 | Study 4 |
|---|---|---|---|
| HLA_DRB1-0703 0.0 | HLA_DRB1-0703 0.0 | HLA_DRB1-0703 0.0 | HLA_DRB1-0703 0.0 |
| HLA_DRB1-0801 0.0206 | HLA_DRB1-0801 0.025 | HLA_DRB1-0801 0.006 | HLA_DRB1-0801 0.0 |
| HLA_DRB1-0802 0.0204 | HLA_DRB1-0802 0.002 | HLA_DRB1-0802 0.004 | HLA_DRB1-0802 0.0 |
| HLA_DRB1-0804 0.0058 | HLA_DRB1-0804 0.002 | HLA_DRB1-0804 0.037 | HLA_DRB1-0804 0.0 |
| HLA_DRB1-0806 0.0004 | HLA_DRB1-0806 0.0 | HLA_DRB1-0806 0.004 | HLA_DRB1-0806 0.0 |
| HLA_DRB1-0813 0.0 | HLA_DRB1-0813 0.0 | HLA_DRB1-0813 0.0 | HLA_DRB1-0813 0.0 |
| HLA_DRB1-0817 0.0 | HLA_DRB1-0817 0.0 | HLA_DRB1-0817 0.0 | HLA_DRB1-0817 0.0 |
| HLA_DRB1-1101 0.0529 | HLA_DRB1-1101 0.057 | HLA_DRB1-1101 0.082 | HLA_DRB1-1101 0.184 |
| HLA_DRB1-1102 0.0063 | HLA_DRB1-1102 0.003 | HLA_DRB1-1102 0.039 | HLA_DRB1-1102 0.0 |
| HLA_DRB1-1104 0.02724 | HLA_DRB1-1104 0.027 | HLA_DRB1-1104 0.01 | HLA_DRB1-1104 0.0 |
| HLA_DRB1-1106 0.00019 | HLA_DRB1-1106 0.0 | HLA_DRB1-1106 0.0 | HLA_DRB1-1106 0.0 |
| HLA_DRB1-1107 0.0 | HLA_DRB1-1107 0.0 | HLA_DRB1-1107 0.0 | HLA_DRB1-1107 0.0 |
| HLA_DRB1-1114 0.0 | HLA_DRB1-1114 0.0 | HLA_DRB1-1114 0.0 | HLA_DRB1-1114 0.0 |
| HLA_DRB1-1120 0.0 | HLA_DRB1-1120 0.0 | HLA_DRB1-1120 0.0 | HLA_DRB1-1120 0.0 |
| HLA_DRB1-1121 0.0 | HLA_DRB1-1121 0.0 | HLA_DRB1-1121 0.0 | HLA_DRB1-1121 0.0 |
| HLA_DRB1-1128 0.0 | HLA_DRB1-1128 0.0 | HLA_DRB1-1128 0.0 | HLA_DRB1-1128 0.0 |
| HLA_DRB1-1301 0.0589 | HLA_DRB1-1301 0.065 | HLA_DRB1-1301 0.067 | HLA_DRB1-1301 0.128 |
| HLA_DRB1-1302 0.0428 | HLA_DRB1-1302 0.043 | HLA_DRB1-1302 0.076 | HLA_DRB1-1302 0.03 |
| HLA_DRB1-1304 0.0011 | HLA_DRB1-1304 0.0 | HLA_DRB1-1304 0.001 | HLA_DRB1-1304 0.0 |
| HLA_DRB1-1305 0.0021 | HLA_DRB1-1305 0.001 | HLA_DRB1-1305 0.0021 | HLA_DRB1-1305 0.0 |
| HLA_DRB1-1307 0.0 | HLA_DRB1-1307 0.0 | HLA_DRB1-1307 0.0 | HLA_DRB1-1307 0.0 |
| HLA_DRB1-1311 0.0002 | HLA_DRB1-1311 0.0 | HLA_DRB1-1311 0.0 | HLA_DRB1-1311 0.0 |
| HLA_DRB1-1321 0.0 | HLA_DRB1-1321 0.0 | HLA_DRB1-1321 0.0 | HLA_DRB1-1321 0.0 |
| HLA_DRB1-1322 0.0 | HLA_DRB1-1322 0.0 | HLA_DRB1-1322 0.0 | HLA_DRB1-1322 0.0 |
| HLA_DRB1-1323 0.0002 | HLA_DRB1-1323 0.0 | HLA_DRB1-1323 0.0 | HLA_DRB1-1323 0.0 |
| HLA_DRB1-1327 0.0 | HLA_DRB1-1327 0.0 | HLA_DRB1-1327 0.0 | HLA_DRB1-1327 0.0 |
| HLA_DRB1-1328 0.0 | HLA_DRB1-1328 0.0 | HLA_DRB1-1328 0.0 | HLA_DRB1-1328 0.0 |
| HLA_DRB1-1501 0.1125 | HLA_DRB1-1501 0.135 | HLA_DRB1-1501 0.027 | HLA_DRB1-1501 0.073 |
| HLA_DRB1-1502 0.00933 | HLA_DRB1-1502 0.008 | HLA_DRB1-1502 0.004 | HLA_DRB1-1502 0.0 |
| HLA_DRB1-1506 9.5e−05 | HLA_DRB1-1506 0.0 | HLA_DRB1-1506 0.0 | HLA_DRB1-1506 0.0 |
| HLA_DRB5-0101 0.0 | HLA_DRB5-0101 0.0 | HLA_DRB5-0101 0.0 | HLA_DRB5-0101 0.0 |
| HLA_DRB5-0105 0.0 | HLA_DRB5-0105 0.0 | HLA_DRB5-0105 0.0 | HLA_DRB5-0105 0.0 |

TABLE 3

| | | | | Weighted sum | | | | | |
|---|---|---|---|---|---|---|---|---|---|
| AA0 | 1 | 2 | 3 | 4 | 5 | 6 | 7 | 8 | |

| | | | | Study 1 | | | | | |
|---|---|---|---|---|---|---|---|---|---|
| A | −742.78148 | 0 | 0 | 0 | 0 | 0 | 0 | 0 | 0 |
| D | −742.78148 | −0.9665825 | −0.9665825 | −0.379388 | 0 | −1.382379 | −0.9579625 | 0 | −0.9119375 |
| E | −742.78148 | 0.0743525 | −0.89223 | −0.651063 | 0 | −1.280535 | −0.3790055 | 0 | −0.7301975 |
| F | −0.371725 | 0.59482 | 0.59482 | 0.355058 | 0 | −0.8073365 | 0.4086345 | 0 | 0.14487 |
| G | −742.78148 | 0.3717625 | 0.148705 | −0.697159 | 0 | −0.4626335 | −0.411656 | 0 | −0.33018 |
| H | −742.78148 | 0.59482 | 0.148705 | 0.2314895 | 0 | −0.4254335 | 0.056161 | 0 | −0.2229395 |
| I | −0.3521 | 0.8178775 | 1.1152875 | 0.409311 | 0 | 0.13634025 | 0.5168511 | 0 | 0.5616875 |
| K | −742.78148 | 0.8178775 | 0 | −0.4342075 | 0 | −0.0855165 | −0.2233845 | 0 | −0.5202525 |
| L | −0.3521 | 0.743525 | 0.743525 | 0.2533155 | 0 | −0.203976 | 0.7543835 | 0 | 0.2357205 |
| M | −0.3521 | 0.8178775 | 1.040935 | 0.494761 | 0 | −0.5799915 | 0.7396835 | 0 | 0.41197 |
| N | −742.78148 | 0.59482 | 0.3717625 | −0.107526 | 0 | −0.0398795 | 0.2012165 | 0 | −0.66987 |
| P | −742.78148 | −0.3717625 | 0.2230575 | −0.8736095 | 0 | 0.08384 | −0.142835 | 0 | −0.6305575 |
| Q | −742.78148 | 0.89223 | 0 | −0.242062 | 0 | −0.573054 | −0.1001245 | 0 | −0.21551 |
| R | −742.78148 | 1.635755 | 0.5204675 | −0.436414 | 0 | −0.026673 | −0.1130545 | 0 | −0.404625 |
| S | −742.78148 | −0.2230575 | 0.148705 | 0.0382325 | 0 | 0.234972 | −0.1686665 | 0 | 0.3417625 |
| T | −742.78148 | 0 | 0 | −0.2190585 | 0 | 0.49565 | −0.177723 | 0 | −0.380445 |
| V | −0.3521 | 1.5614025 | 0.3717625 | 0.040327 | 0 | 0.4902615 | 0.1548225 | 0 | 0.1675575 |
| W | −0.391425 | −0.0743525 | 0 | −0.2236815 | 0 | −0.823982 | 0.012708 | 0 | −0.552675 |
| Y | −0.391425 | 0.6691725 | 0.59482 | 0.0221735 | 0 | −0.798447 | 0.1061515 | 0 | −0.1662225 |
| C | −742.78148 | 0 | 0 | 0 | 0 | 0 | 0 | 0 | 0 |

| | | | | Study 2 | | | | | |
|---|---|---|---|---|---|---|---|---|---|
| A | −783.216 | 0 | 0 | 0 | 0 | 0 | 0 | 0 | 0 |
| D | −783.216 | −1.0192 | −1.0192 | −0.3147 | 0 | −1.4193 | −0.9492 | 0 | −0.9588 |
| E | −783.216 | 0.0784 | −0.9408 | −0.6463 | 0 | −1.686 | 0 | −0.7614 | |
| F | −0.403 | 0.6272 | 0.6272 | 0.36492 | 0 | −0.8262 | 0.4655 | 0.0 | 0.1852 |
| G | −783.216 | 0.392 | 0.1568 | −0.7046 | 0 | −0.4776 | −0.4156 | 0 | −0.3362 |
| H | −783.216 | 0.6272 | 0.1568 | 0.303 | 0 | −0.4511 | 0.0841 | −0.25386 | |
| I | −0.367 | 0.8624 | 1.176 | 0.44398 | 0 | 0.14185 | 0.5939 0.0 40.0 | 0.6236 | |
| K | −783.216 | 0.8624 | 0 | −0.5322 | 0 | −0.1239 | −0.2222 | 0 | −0.56 |
| L | −0.367 | 0.784 | 0.784 | 0.2509 | 0 | −0.2129 | 0.8405 | 0 | 0.2851 |
| M | −0.367 | 0.8624 | 1.0976 | 0.4934 | 0 | −0.5918 | 0.83086 | 0 | 0.45876 |
| N | −783.216 | 0.6272 | 0.392 | −0.10134 | 0 | −0.0084 | 0.25841 | 0 | −0.6994 |
| P | −783.216 | −0.392 | 0.2352 | −0.9084 | 0 | 0.0756 | −0.11557 | 0 | −0.6526 |
| Q | −783.216 | 0.9408 | 0 | −0.243 | 0 | −0.6121 | −0.078 0.0 | −0.2579 | |
| R | −783.216 | 1.7248 | 0.5488 | −0.5148 | 0 | −0.039 | −0.13624 | 0 | −0.4126 |
| S | −783.216 | −0.2352 | 0.1568 | 0.0963 | 0 | 0.271 | −0.14233 | 0 | 0.3518 |
| T | −783.216 | 0 | 0 | −0.1873 | 0 | 0.52682 | −0.13014 | 0 | −0.3828 |
| V | −0.367 | 1.6464 | 0.392 | 0.0304 | 0 | 0.5042 | 0.19798 | 0 | 0.2042 |
| W | −0.417 | −0.0784 | 0 | −0.2532 | 0 | −0.843 | 0.0310 80.0 | −0.5804 | |
| Y | −0.417 | 0.7056 | 0.6272 | −0.0118 | 0 | −0.8107 | 0.1336 50.0 | −0.1569 | |
| C | −783.216 | 0 | 0 | 0 | 0 | 0 | 0 | 0 | 0 |

| | | | | Study 3 | | | | | |
|---|---|---|---|---|---|---|---|---|---|
| A | −540.5589 | 0 | 0 | 0 | 0 | 0 | 0 | 0 | 0 |
| D | −540.5589 | −0.70343 | −0.70343 | −0.70117 | 0 | −1.17584 | −0.90597 | 0 | −0.66036 |
| E | −540.5589 | 0.05411 | −0.64932 | −0.57337 | 0 | −0.93374 | −0.41443 | 0 | −0.53133 |
| F | −0.205 | 0.43288 | 0.43288 | 0.31248 | 0 | −0.67664 | 0.23656 | 0 | 0.06589 |
| G | −540.5589 | 0.27055 | 0.10822 | −0.72177 | 0 | −0.36857 | −0.45304 | 0 | −0.25546 |
| H | −540.5589 | 0.43288 | 0.10822 | 0.18694 | 0 | −0.27531 | 0.07708 | 0 | −0.11113 |
| I | −0.3031 | 0.59521 | 0.81165 | 0.17641 | 0 | 0.12082 | 0.22304 | 0 | 0.35726 |
| K | −540.5589 | 0.59521 | 0 | −0.07825 | 0 | 0.11283 −0.08342 | 0 | −0.32352 | |
| L | −0.3031 | 0.5411 | 0.5411 | 0.23841 | 0 | −0.13828 | 0.48855 | 0 | 0.099516 |
| M | −0.3031 | 0.59521 | 0.75754 | 0.4174 | 0 | −0.48929 | 0.3653 | 0 | 0.26883 |
| N | −540.5589 | 0.43288 | 0.27055 | −0.08228 | 0 | −0.18496 | 0.04292 | 0 | −0.49966 |
| P | −540.5589 | −0.27055 | 0.16233 | −0.74947 | 0 | 0.10925 | −0.215095 | 0 | −0.47333 |
| Q | −540.5589 | 0.64932 | 0 | −0.11094 | 0 | −0.36933 | −0.14821 | 0 | −0.06722 |
| R | −540.5589 | 1.19042 | 0.37877 | −0.19197 | 0 | 0.0607 | 0.14523 | 0 | −0.30325 |
| S | −540.5589 | −0.16233 | 0.10822 | −0.13507 | 0 | 0.07839 | −0.30669 | 0 | 0.28761 |
| T | −540.5589 | 0 | 0 | −0.24596 | 0 | 0.33226 | −0.31236 | 0 | −0.32225 |
| V | −0.3031 | 1.13631 | 0.27055 | −0.03911 | 0 | 0.41402 | 0.03914 | 0 | 0.07203 |
| W | −0.238 | −0.05411 | 0 | −0.05011 | 0 | −0.69214 | 0.05772 | 0 | −0.3894 |
| Y | −0.238 | 0.48699 | 0.43288 | 0.02693 | 0 | −0.69324 | 0.02116 | 0 | −0.13537 |

| | | | | Study 4 | | | | | |
|---|---|---|---|---|---|---|---|---|---|
| A | −671.328 | 0 | 0 | 0 | 0 | 0 | 0 | 0 | 0 |
| D | −671.328 | −0.8736 | −0.8736 | −0.2481 | 0 | −1.3892 | −0.9591 | 0 | −0.8045 |

TABLE 3-continued

| | | | | Weighted sum | | | | |
|---|---|---|---|---|---|---|---|---|
| AA0 | 1 | 2 | 3 | 4 | 5 | 6 | 7 | 8 |
| E | −671.328 | 0.0672 | −0.8064 | −0.6498 | 0 | −1.4497 | 0 | −0.6656 |
| F | −0.338 | 0.5376 | 0.5376 | 0.1918 | 0 | −0.8077 | 0.2455 | 0.1059 |
| G | −671.328 | 0.336 | 0.1344 | −0.6453 | 0 | −0.4284 | −0.3801 | −0.222 |
| H | −671.328 | 0.5376 | 0.1344 | 0.2829 | 0 | −0.2188 | −0.0048 | −0.21916 |
| I | −0.334 | 0.7392 | 1.008 | 0.2959 | 0 | 0.30455 | 0.37202 | 0.3441 |
| K | −671.328 | 0.7392 | 0 | −0.3353 | 0 | 0.3856 | −0.1732 | −0.3191 |
| L | −0.334 | 0.672 | 0.672 | 0.3085 | 0 | −0.0104 | 0.6733 | −0.0329 |
| M | −0.334 | 0.7392 | 0.9408 | 0.4186 | 0 | −0.539 | 0.666 | 0.34314 |
| N | −671.328 | 0.5376 | 0.336 | 0.0246 | 0 | −0.1867 | −0.01263 | −0.6398 |
| P | −671.328 | −0.336 | 0.2016 | −0.8783 | 0 | 0.1969 | −0.0264 | −0.5248 |
| Q | −671.328 | 0.8064 | 0 | −0.07 | 0 | −0.3597 | −0.2396 | −0.1022 |
| R | −671.328 | 1.4784 | 0.4704 | −0.4028 | 0 | 0.3368 | −0.0814 | −0.2183 |
| S | −671.328 | −0.2016 | 0.1344 | −0.0144 | 0 | 0.0935 −0.34031 | 0 | 0.4594 |
| T | −671.328 | 0 | 0 | −0.3199 | 0 | 0.4974 | −0.3365 | −0.4373 |
| V | −0.334 | 1.4112 | 0.336 | −0.0612 | 0 | 0.6161 | 0.01782 | 0.0488 |
| W | −0.338 | −0.0672 | 0 | −0.154 | 0 | −0.8142 | −0.06 | −0.6004 |
| Y | −0.338 | 0.6048 | 0.5376 | −0.1729 | 0 | −0.7934 | −0.04255 | −0.1636 |
| C | −671.328 | 0 | 0 | 0 | 0 | 0 | 0 | 0 |

TABLE 4

| Study 1: Optimal sequence: (binding position, AA, sum score) | | |
|---|---|---|
| 0 | I | −0.3521 |
| 1 | R | 1.635755 |
| 2 | I | 1.1152875 |
| 3 | M | 0.494761 |
| 4 | A | 0 |
| 5 | T | 0.49565 |
| 6 | L | 0.7543835 |
| 7 | A | 0 |
| 8 | I | 0.5616875 |
| Study 2: Optimal sequence: (binding position, AA, sum score) | | |
| 0 | I | −0.367 |
| 1 | R | 1.7248 |
| 2 | I | 1.176 |
| 3 | M | 0.4934 |
| 4 | A | 0 |
| 5 | T | 0.52682 |
| 6 | L | 0.8405 |
| 7 | A | 0 |
| 8 | I | 0.6236 |
| Study 3: Optimal sequence: (binding position, AA, sum score) | | |
| 0 | F | −0.205 |
| 1 | R | 1.19042 |
| 2 | I | 0.81165 |
| 3 | M | 0.4174 |
| 4 | A | 0 |
| 5 | V | 0.41402 |
| 6 | L | 0.48855 |
| 7 | A | 0 |
| 8 | I | 0.35726 |
| Study 4: Optimal sequence: (binding position, AA, sum score) | | |
| 0 | I | −0.334 |
| 1 | R | 1.4784 |
| 2 | I | 1.008 |
| 3 | M | 0.4186 |
| 4 | A | 0 |
| 5 | V | 0.6161 |
| 6 | L | 0.6733 |
| 7 | A | 0 |
| 8 | S | 0.4594 |

Example 5

Effect of TLR Activation on CLIP Expression in γδ T and B Cells

Methods and Results:

As it was found that TLR3 and TLR7 activation causes PE-like symptoms in mice, the ability of TLR activation to increase CLIP expression on γδ T and B cells was examined. We previously showed that in vitro treatment with various TLR agonists markedly increased CLIP expression on mouse splenic γδ T and B cells and this effect was absent in B cells from CLIP KO mice. Furthermore, in vitro activation of TLRs in human peripheral blood mononuclear cells (PBMCs) significantly increased CLIP+B cell levels. (Newell J Leukoc Biol 2010)

Example 6

In Vivo Effect of TLR Activation Via TLR3 or TLR7 in γδ T and B Cells

Figure 11A:
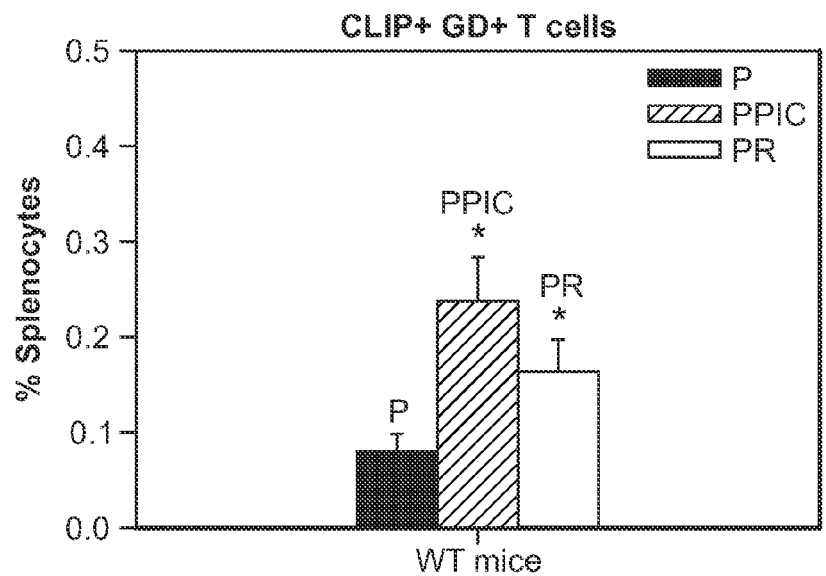
FIGS. 11A and 11B are a set of graphs depicting Splenic levels in CLIP+GD+T cells and CD 19+B cells.
Figure 11B:
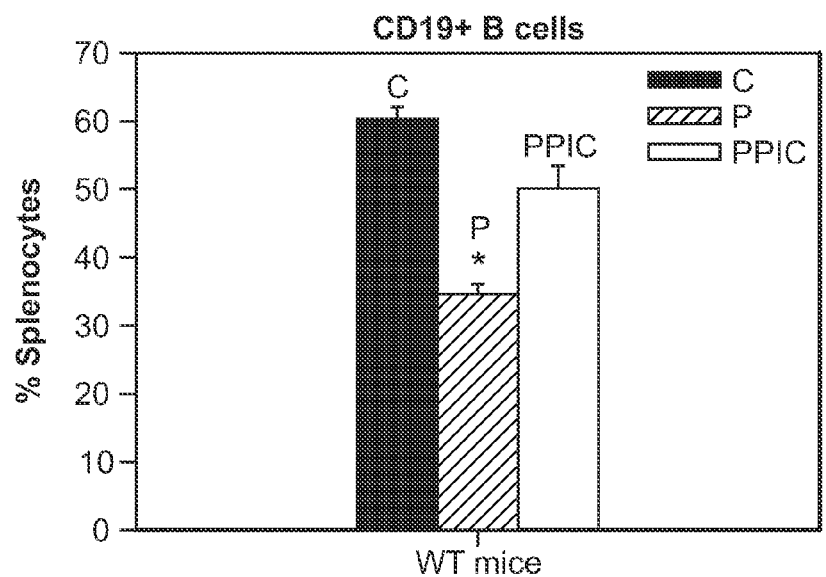

Methods and Results:

Next, it was important to determine whether this effect also happens in vivo. Therefore, we tested whether TLR activation via TLR3 or TLR7, which cause PE in mice only if they are pregnant, increases splenic CLIP+γδ T and B cells in mice. FIG. 11 demonstrates that CLIP+γδ T cells were increased significantly in pregnant (P) mice made hypertensive by the TLR3 agonist poly I:C (PPIC) or by the TLR7 agonist R837 (PR). With respect to B cells in general, a dramatic increase in B cell death was found during normal pregnancy; however mice with PE induced by TLR3 activation did not experience the increase in B cell death (FIG. 11).

As CLIP expression induced by TLR activation was found to prevent T and B cell death, it was indicated that CLIP removal may increase cell death following TLR activation. It was shown that MHC class II engagement, in the absence of antigen receptor engagement, can lead to the death of APCs including B cells. Since TLR-mediated activation of B cells results in ectopic CLIP expression (FIGS. 11 and 12) we sought to determine whether CLIP serves as a negative regulator of B cell death. To test this mouse splenic B cells from C57B16 mice or CLIP KO mice were activated, with or without a TLR agonist, for 48 hrs. As shown in FIG. 11 (Left) splenic levels of CLIP+γδ T cells were increased significantly in PE mice (PPIC and PR) compared to vehicle-treated pregnant controls (P). The data shown in the right panel of FIG. 11 shows a decrease in splenic B cells in normal pregnant mice (P), which was absent in PE mice (PPIC). Splenocytes were analyzed by flow cytometry.

Figure 12:
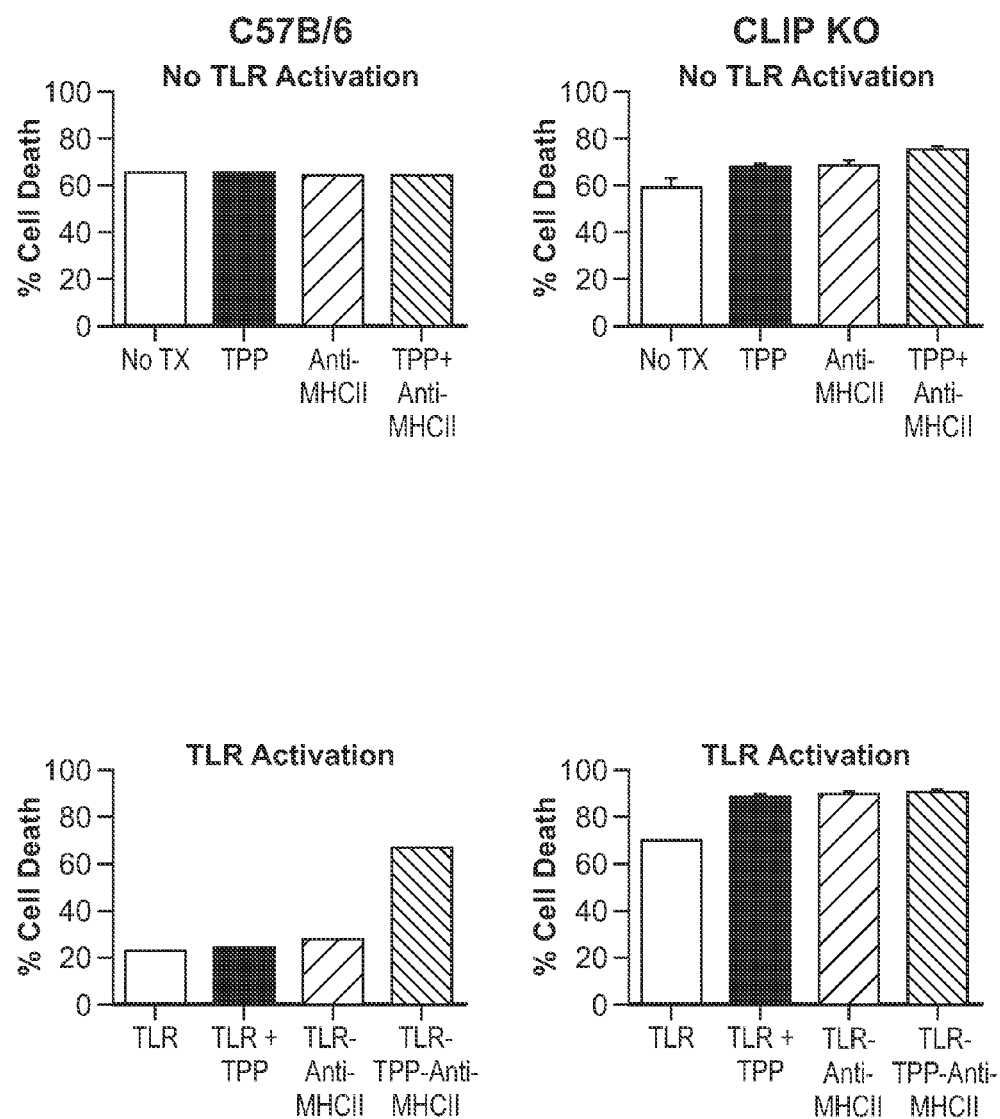
FIG. 12 is a set of graphs depicting in vitro treatment with CLIP-displacing peptide TPP and with or without a TLR agonist. B cells isolated from control and CLIP KO mice were treated in vitro with the CLIP-displacing peptide TPP and with or without a TLR agonist. Some of the cells were then treated with anti-MHC class II in order to stimulate cell death. Only B cells activated non-specifically by a TLR agonist and that did not express CLIP exhibited a marked increase in MHC class II-mediated cell death. This effect was absent in B cells isolated from CLIP KO mice.

The cultured cells were then treated with TPP to displace CLIP or vehicle followed by an antibody to MHC class II. As shown in FIG. 12, TPP treatment increased susceptibility to MHC II-mediated cell death in the TLR-activated cells from WT mice, but not in CLIP KO mice. B cells isolated from control and CLIP KO mice were treated in vitro with the CLIP-displacing peptide TPP and with or without a TLR agonist. Some of the cells were then treated with anti-MHC class II in order to stimulate cell death. Only B cells activated non-specifically by a TLR agonist and that did not express CLIP exhibited a marked increase in MHC class II-mediated cell death. This effect was absent in B cells isolated from CLIP KO mice, as shown in FIG. 12.

Example 7

The Role of TCR Specificity in MHC II-Mediated B Cell Death

Figure 13:
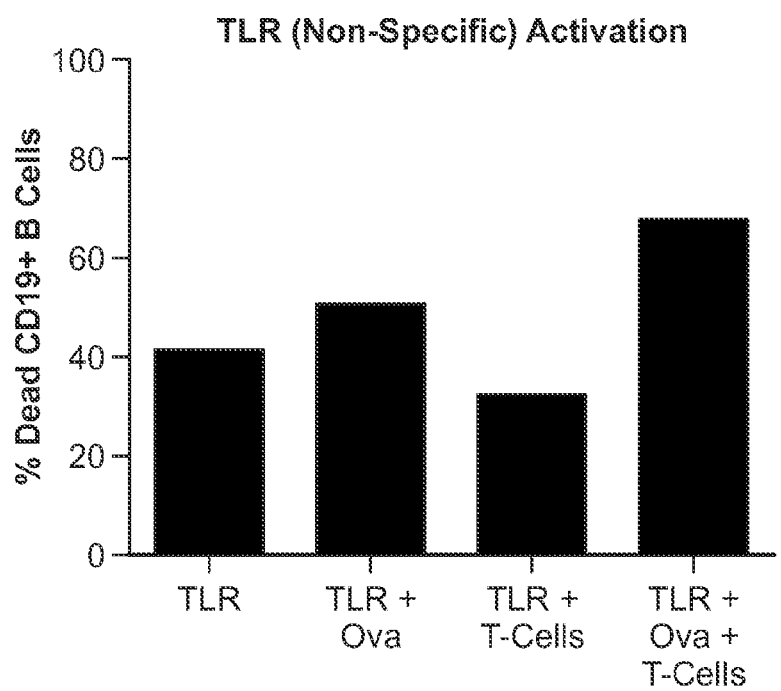
FIG. 13 is a set of graphs depicting percentages of dead CD19+B cells from groups activated specifically and non-specifically. B cells isolated from control mice were activated non-specifically with a TLR agonist or specifically with an antigen mimic (Anti-Ig) and then incubated with or without mutant T cells that bind Ova peptide in the MHC class II groove instead of CLIP.
Figure 13:
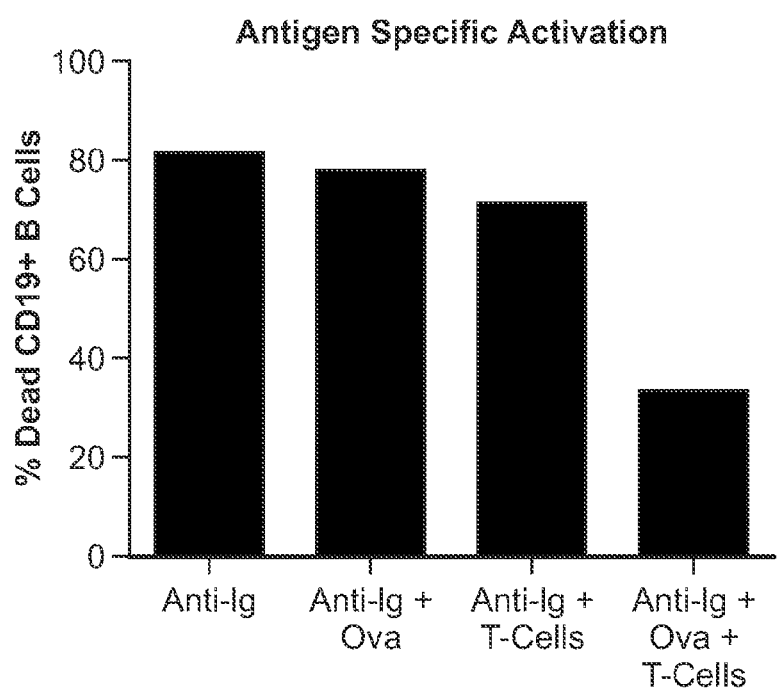

Methods and Results:

To confirm the role of TCR specificity in MHC II-mediated B cell death, the T cell hybridoma MF2.2D9 was obtained from Dr. Ken Rock (Harvard University). MF2.2D9 T cells are a CD4+T-cell hybridoma with a TCR specific for an ovalbumin peptide consisting of amino acids 257-264 in the mouse MHC II molecule I-A$^b$. These cells were co-cultured with resting B cells that express I-A$^b$ isolated from C57B/6 mice. The resting B cells were activated with a TLR agonist (non-specific activation) or with anti-IgM+IL-4 as a surrogate for BCR engagement (specific activation). After 48 hrs of activation, cells were seeded with OVa$_{257\text{-}264}$ and incubated for 4 hrs. Next, the B cells were co-cultured with the MF2.2D9 T cells for 24 hrs and then all cells were stained for CD19+(B cells) and analyzed by flow cytometry. Forward vs. side scatter gating of CD19+cells was used to determine B cell death, with decreased forward scatter and increased side scatter indicative of B cell death. Results shown in FIG. 13 suggested that upon engagement with the TCR, non-specifically activated B cells that do not express CLIP die (TLR+ Ova+T cells), while B cells that have been specifically activated by antigen remain alive (Anti-Ig+Ova+T cells).

Figure 14:
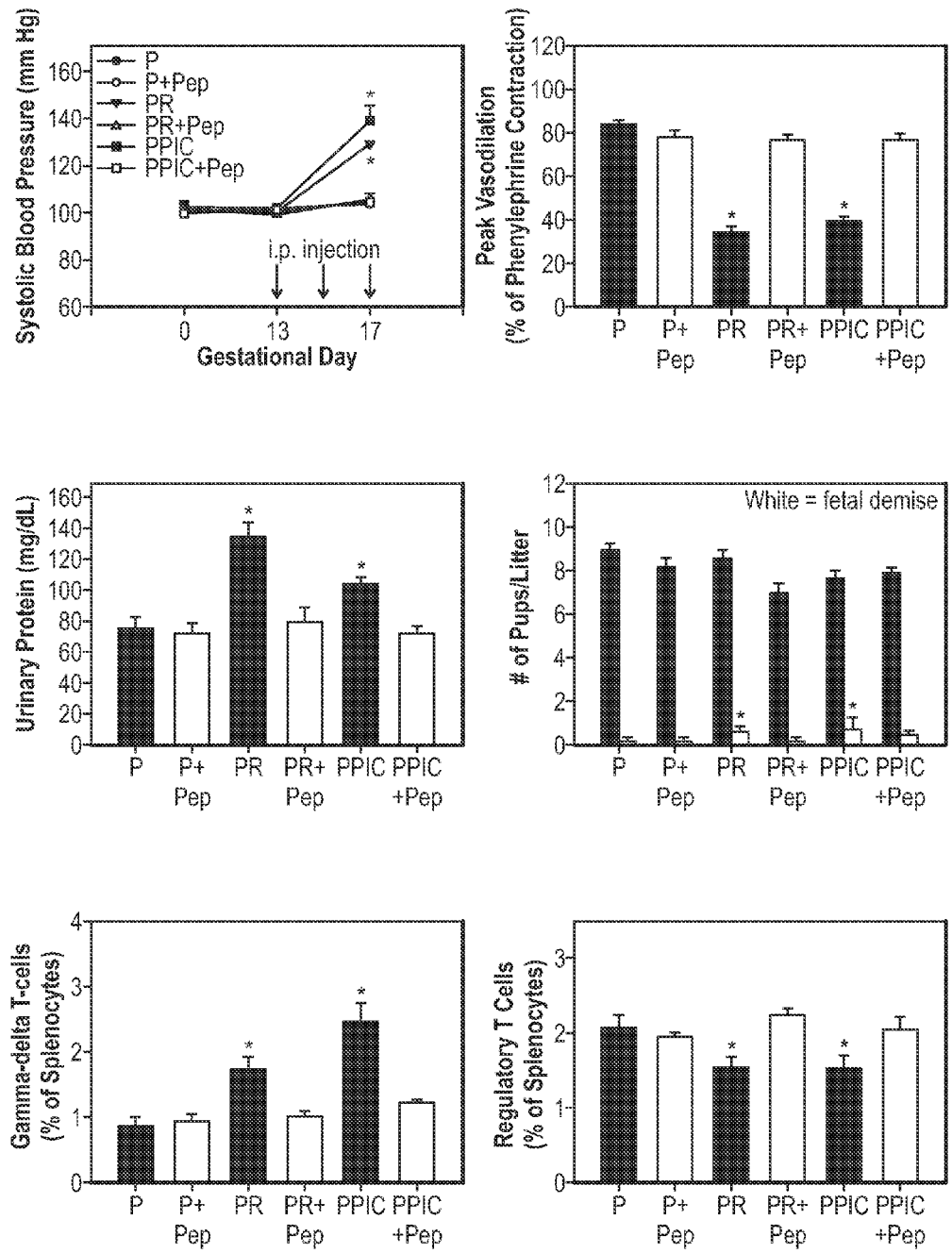
FIG. 14 is a series of graphs depicting results from the daily administration of the CLIP-displacing peptide TPP. Daily administration of the CLIP-displacing peptide TPP ("Pep"-gestational days 13-17) prevented the development of hypertension, endothelial dysfunction, proteinuria, fetal demise, increased γδT cells, and decreased regulatory T cells in pregnant (P) mice treated with the TLR7 agonist R837 (PR mice) or the TLR3 agonist poly I:C (PPIC mice) on gestational days 13, 15, and 17.

TPP was utilized to displace CLIP on immune cells in mice during pregnancy. In pregnant mice with PE induced by TLR3 or TLR7 activation, daily administration of TPP at the onset of TLR agonist treatment on gestational day 13 completely prevented the development of PE and its associated effects characteristic of those seen in women with PE (FIG. 14). The results also demonstrated that TPP is safe in mice and has no side effects on the mother or the pups.

Example 8

Analysis of TPP as a Therapeutic for PE

Figure 15:
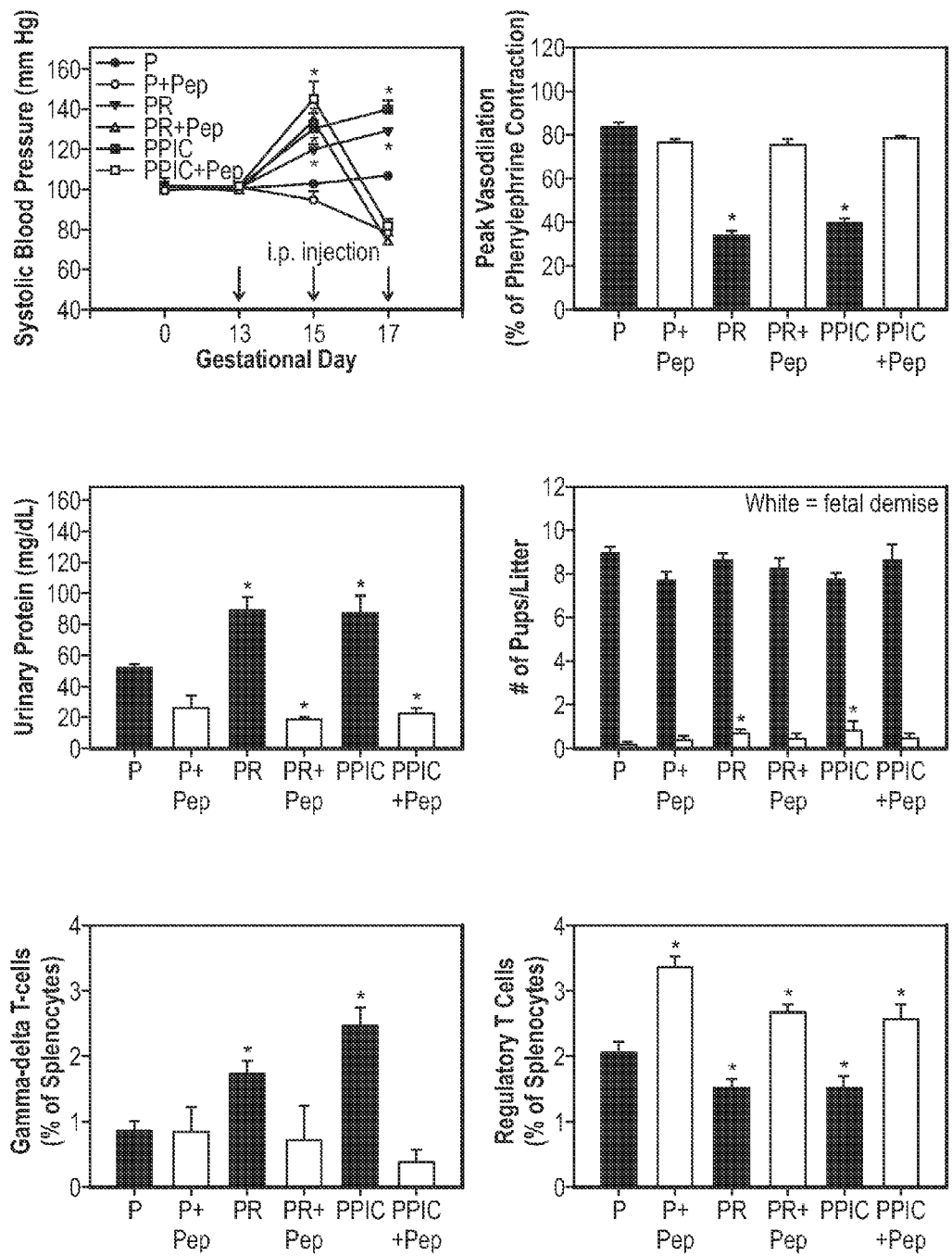
FIG. 15 is a series of graphs depicting results from the daily administration of TPP. Daily administration of TPP ("Pep"-gestational days 15-17) ameliorated the hypertension, endothelial dysfunction, proteinuria, fetal demise, increased γδ T cells, and decreased regulatory T cells in pregnant (P) mice treated with the TLR7 agonist R837 (PR mice) or the TLR3 agonist poly I:C (PPIC mice) on gestational days 13, 15, and 17.

Methods and Results:

Next, TPP was tested as a therapeutic for PE. Therefore it was determined whether CLIP displacement could ameliorate PE once established in mice. TLR agonists were administered on gestational days 13, 15, and 17 as above, however TPP treatment on gestational day 15 was initiated once mice were hypertensive instead of day 13. TPP peptide treatment on gestational days 15-17 was able to significantly reduce systolic blood pressure, endothelial dysfunction, proteinuria, fetal demise, and γδ T cells while increasing anti-inflammatory regulatory T cells in PE mice (FIG. 15). Daily administration of TPP ("Pep"-gestational days 15-17) ameliorated the hypertension, endothelial dysfunction, proteinuria, fetal demise, increased γδ T cells, and decreased regulatory T cells in pregnant (P) mice treated with the TLR7 agonist R837 (PR mice) or the TLR3 agonist poly I:C (PPIC mice) on gestational days 13, 15, and 17, as shown in FIG. 15.

Together, these data demonstrate that TLR activation increases CLIP expression on pro-inflammatory γδ T cells and B cells leading to protection from cell death, persistent activation, inflammation, and PE. A targeted peptide that depletes CLIP+immune cells (i.e., γδ T and B cells) may both prevent PE in mice as well as ameliorate PE once developed in mice. The data definitively demonstrate that CLIP peptides are useful for reducing blood pressure and treating preeclampsia.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating a subject having preeclampsia, comprising administering to the subject an isolated CLIP inhibitor in an effective amount to reduce the blood pressure in the subject with respect to blood pressure levels prior to treatment.

2. A method, comprising administering to a subject having high blood pressure an isolated CLIP inhibitor in an effective amount to reduce the blood pressure in the subject with respect to blood pressure levels prior to treatment.

3. The method of claim 1, wherein CLIP inhibitor is synthetic.

4. The method of claim 1, wherein CLIP inhibitor is a TNP peptide.

5. The method of claim 1, wherein the CLIP inhibitor is an MHC class II CLIP inhibitor.

6. The method of claim 1, wherein CLIP inhibitor is a peptide, wherein the peptide comprises FRIM $X_4$VL$X_6$S (SEQ ID NO: 6), wherein $X_4$ and $X_6$ are any amino acid.

7. The method of claim 1, wherein CLIP inhibitor is a peptide, wherein the peptide comprises FRIMAVLAS (SEQ ID NO: 2).

8. The method of claim 1, wherein CLIP inhibitor is a peptide, wherein the peptide comprises IRIMATLAI (SEQ ID NO: 4).

9. The method of claim 1, wherein CLIP inhibitor is a peptide, wherein the peptide comprises FRIMAVLAI (SEQ ID NO: 10).

10. The method of claim 1, wherein CLIP inhibitor is a peptide, wherein the peptide comprises IRIMAVLAS (SEQ ID NO: 11).

11. The method of claim 2, wherein the subject has heart disease.

12. The method of claim 1, wherein the CLIP inhibitor is administered to the subject after diagnosis of preeclampsia or high blood pressure.

13. A composition comprising IRIMATLAI (SEQ ID NO: 4), FRIMAVLAI (SEQ ID NO: 10), or IRIMAVLAS (SEQ ID NO: 11).

* * * * *

SEQUENCE LISTING

<160> NUMBER OF SEQ ID NOS: 88

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

```
Met Arg Met Ala Thr Pro Leu Leu Met
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

Phe Arg Ile Met Ala Val Leu Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid

<400> SEQUENCE: 3

Xaa Arg Xaa Xaa Xaa Xaa Leu Xaa Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 4

Ile Arg Ile Met Ala Thr Leu Ala Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Phe Arg Ile Met Ala Val Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa can be any amino acid
```

```
<220> FEATURE:
<221> NAME/KEY: MISC_FEATURE
<222> LOCATION: (8)..(8)
<223> OTHER INFORMATION: Xaa can be any amino acid

<400> SEQUENCE: 6

Phe Arg Ile Met Xaa Val Leu Xaa Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Phe Arg Ile Met Ala Val Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa can be Ala, Phe, Met, Leu, Ile, Val, Pro or
      Trp
<220> FEATURE:
<221> NAME/KEY: MISC_FEATURE
<222> LOCATION: (3)..(4)
<223> OTHER INFORMATION: Xaa can be Ala, Phe, Met, Leu, Ile, Val, Pro or
      Trp
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be Ala, Phe, Met, Leu, Ile, Val, Pro or
      Trp
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be Ala, Cys, Thr, Ser, Gly, Asn, Gln or
      Tyr

<400> SEQUENCE: 8

Xaa Arg Xaa Xaa Xaa Xaa Leu Xaa Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (3)..(6)
<223> OTHER INFORMATION: Xaa can be any amino acid
```

```
<220> FEATURE:
<221> NAME/KEY: MISC_FEATURE
<222> LOCATION: (8)..(9)
<223> OTHER INFORMATION: Xaa can be any amino acid

<400> SEQUENCE: 9

Xaa Arg Xaa Xaa Xaa Xaa Leu Xaa Xaa
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Phe Arg Ile Met Ala Val Leu Ala Ile
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 11

Ile Arg Ile Met Ala Val Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 12

Leu Val Gln Asn Asp Thr Leu Leu Gln
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 13

Val Val Ser Thr Gln Thr Ala Leu Ala
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 14

Ile Met Asn Ser Phe Val Asn Asp Ile
1               5

<210> SEQ ID NO 15
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 15

Met Gly Ile Met Lys Ser Phe Val Asn
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 16

Met Gly Ile Met Asn Ser Phe Val Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

Val Leu Ile Ala Phe Ser Gln Tyr Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 18

Ile Met Asn Ser Phe Val Asn Asp Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 19

Ile Met Lys Ser Phe Val Asn Asp Ile
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 20

Ile Gln Gly Ile Thr Lys Pro Ala Ile
1               5

<210> SEQ ID NO 21
<211> LENGTH: 9
<212> TYPE: PRT
<213> ORGANISM: Artificial Sequence
```

<220> FEATURE:
<223> OTHER INFORMATION: Synthetic Polypeptide

<400> SEQUENCE: 21

Val Thr Ala Met Asp Val Val Tyr Ala
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 22

Tyr Gly Phe Gln Asn Ala Leu Ile Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 23

Leu Val Asn Glu Leu Thr Glu Phe Ala
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 24

Phe Gln Asn Ala Leu Ile Val Arg Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

Met Ser Ile Met Asn Ser Phe Val Asn
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 26

Leu Val Leu Ile Ala Phe Ser Gln Tyr
1               5

<210> SEQ ID NO 27
<211> LENGTH: 9
<212> TYPE: PRT
<213> ORGANISM: Artificial Sequence
<220> FEATURE:

```
<223> OTHER INFORMATION: Synthetic Polypeptide

<400> SEQUENCE: 27

Val Gln Asn Asp Thr Leu Leu Gln Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 28

Met Gly Asn Met Asn Ser Phe Val Asn
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 29

Phe Gln Ser Ala Ile Lys Leu Val Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 30

Val Ala Phe Val Asp Lys Cys Cys Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 31

Leu Val Val Ser Thr Gln Thr Ala Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Val Phe Leu Glu Asn Val Ile Arg Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 33

Leu Ile Ala Phe Ser Gln Tyr Leu Gln
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 34

Phe Gln Ser Ala Ala Ile Gly Ala Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 35

Met Asp Ile Met Asn Ser Phe Val Asn
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 36

Ile Lys Leu Val Asp Phe Gln Asp Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 37

Val Met Glu Asn Phe Val Ala Phe Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 38

Tyr Leu Gln Gln Cys Pro Phe Asp Glu
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 39

Val Leu Pro Asn Ile Gln Ala Val Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 40

Val Glu Pro Ser Asp Thr Ile Glu Asn
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 41

Phe Phe Gln Ser Ala Ile Lys Leu Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Ile Gln Ala Val Leu Leu Pro Lys Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

Ile Ala Phe Ser Gln Tyr Leu Gln Gln
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 44

Phe Leu Gly Ser Phe Leu Tyr Glu Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 45

```
Phe Val Asn Asp Ile Phe Glu Arg Ile
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 46

```
Leu Pro Asn Ile Gln Ala Val Leu Leu
1               5
```

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 47

```
Leu Leu Pro Gly Glu Leu Ala Lys His
1               5
```

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 48

```
Phe Val Ala Phe Val Asp Lys Cys Cys
1               5
```

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

```
Leu Lys Pro Asp Pro Asn Thr Leu Cys
1               5
```

<210> SEQ ID NO 50
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 50

```
Met Glu Asn Phe Val Ala Phe Val Asp
1               5
```

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 51

```
Leu Phe Gly Asp Glu Leu Cys Lys Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Val Thr Ile Ala Gln Gly Gly Val Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Met Lys Ser Phe Val Asn Asp Ile Phe
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 54

Leu Phe Thr Phe His Ala Asp Ile Cys
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 55

Phe Val Asn Asp Leu Phe Glu Arg Leu
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 56

Ile Ala Gln Gly Gly Val Leu Pro Asn
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 57

Leu Gly Ser Phe Leu Tyr Glu Tyr Ser
```

```
<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

Phe Val Asp Lys Cys Cys Ala Ala Asp
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 59

Leu Phe Glu Asp Thr Asn Leu Cys Ala
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 60

Val Asn Phe Ala Glu Phe Ser Lys Lys
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 61

Met Asn Ser Phe Val Asn Asp Ile Phe
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 62

Met Asn Ser Phe Val Asn Asp Leu Phe
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 63

Leu Val Asp Glu Pro Gln Asn Leu Ile
1               5
```

<210> SEQ ID NO 64
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 64

Met Asp Val Val Tyr Ala Leu Lys Arg
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 65

Leu Leu Leu Pro Gly Glu Leu Ala Lys
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 66

Leu Thr Pro Asp Glu Thr Tyr Val Pro
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 67

Leu Gln Asn Glu Ile Asp Val Ser Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 68

Leu Val Asp Phe Gln Asp Ala Lys Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 69

Val Gly Leu Phe Glu Asp Thr Asn Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 70

Leu Gly Leu Ile Tyr Glu Glu Thr Arg
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 71

Ile Leu Gly Leu Ile Tyr Glu Glu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 72

Ile Asp Val Ser Ser Arg Glu Lys Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 73

Leu His Thr Leu Phe Gly Asp Glu Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 74

Leu Val Gly Leu Phe Glu Asp Thr Asn
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 75

Ile Ala Gln Asp Phe Lys Thr Asp Leu
1               5

```
<210> SEQ ID NO 76
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 76

Phe His Ala Asp Ile Cys Thr Leu Pro
1               5

<210> SEQ ID NO 77
<211> LENGTH: 1155
<212> TYPE: DNA
<213> ORGANISM: Artificial Sequence
<220> FEATURE:
<223> OTHER INFORMATION: Synthetic Polynucleotide

<400> SEQUENCE: 77 ccgggggtc agggtcccag atgcacagga ggagaagcag gagctgtcgg gaagatcaga      60
agccagtcat ggatgaccag cgcgacctta tctccaacaa tgagcaactg cccatgctgg    120
gccggcgccc tggggccccg gagagcaagt gcagccgcgg agccctgtac acaggctttt    180
ccatcctggt gactctgctc ctcgctggcc aggccaccac cgcctacttc ctgtaccagc    240
agcagggccg gctggacaaa ctgacagtca cctcccagaa cctgcagctg gagaacctgc    300
gcatgaagct tcccaagcct cccaagcctg tgagcaagat gcgcatggcc accccgctgc    360
tgatgcaggc gctgcccatg ggagccctgc cccaggggcc catgcagaat gccaccaagt    420
atggcaacat gacagaggac catgtgatgc acctgctcca gagtcactgg aactggagga    480
cccgtcttct gggctgggtg tgaccaagca ggatctgggc ccagtcccca tgtgagagca    540
gcagaggcgg tcttcaacat cctgccagcc cacacagct acagctttct tgctcccttc    600
agcccccagc cctcccccca tctcccaccc tgtacctcat cccatgagac cctggtgcct    660
ggctctttcg tcacccttgg acaagacaaa ccaagtcgga acagcagata caatgcagc    720 aaggccctgc tgcccaatct ccatctgtca acagggcgt gaggtcccag gaagtggcca    780
aaagctagac agatccccgt tcctgacatc acagcagcct ccaacacaag gctccaagac    840
ctaggctcat ggacgagatg ggaaggcaca gggagaaggg ataaccctac acccagaccc    900
caggctggac atgctgactg tcctctcccc tccagccttt ggccttggct tttctagcct    960
atttacctgc aggctgagcc actctcttcc ctttccccag catcactccc caaggaagag   1020
ccaatgtttt ccaccataa tcctttctgc cgacccctag ttccctctgc tcagccaagc   1080
ttgttatcag ctttcagggc catggttcac attagaataa aaggtagtaa ttagaacaaa   1140
aaaaaaaaaa aaaaa                                                   1155

<210> SEQ ID NO 78
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 78
gguaguaauu agaacaaaa                                                19

<210> SEQ ID NO 79
<211> LENGTH: 19
<212> TYPE: RNA
<213> ORGANISM: Artificial Sequence
```

-continued

```
<220> FEATURE:
<223> OTHER INFORMATION: Synthetic Polynucleotide

<400> SEQUENCE: 79
gguucacauu agaauaaaa                                                  19

<210> SEQ ID NO 80
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 80
gaacaaaaaa aaaaaaaaa                                                  19

<210> SEQ ID NO 81
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 81
caaaaaaaaa aaaaaaaaa                                                  19

<210> SEQ ID NO 82
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 82
agaacaaaaa aaaaaaaaa                                                  19

<210> SEQ ID NO 83
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 83
acaaaaaaaa aaaaaaaaa                                                  19

<210> SEQ ID NO 84
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 84
guaauuagaa caaaaaaa                                                   19

<210> SEQ ID NO 85
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 85
caugguucac auuagaaua                                                  19
```

<210> SEQ ID NO 86
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 86
guaguaauua gaacaaaaa                                                    19

<210> SEQ ID NO 87
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 87
ggcuuuucua gccuauuua                                                    19

<210> SEQ ID NO 88
<211> LENGTH: 295
<212> TYPE: PRT
<213> ORGANISM: Artificial Sequence
<220> FEATURE:
<223> OTHER INFORMATION: Synthetic Polypeptide

<400> SEQUENCE: 88

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Pro Lys Pro Val Ser Lys Met Arg Met Ala Thr Pro Leu
            100                 105                 110

Leu Met Gln Ala Leu Pro Met Gly Ala Leu Pro Gln Gly Pro Met Gln
        115                 120                 125

Asn Ala Thr Lys Tyr Gly Asn Met Thr Glu Asp His Val Met His Leu
    130                 135                 140

Leu Gln Asn Ala Asp Pro Leu Lys Val Tyr Pro Pro Leu Lys Gly Ser
145                 150                 155                 160

Phe Pro Glu Asn Leu Arg His Leu Lys Asn Thr Met Glu Thr Ile Asp
                165                 170                 175

Trp Lys Val Phe Glu Ser Trp Met His His Trp Leu Leu Phe Glu Met
            180                 185                 190

Ser Arg His Ser Leu Glu Gln Lys Pro Thr Asp Ala Pro Pro Lys Val
        195                 200                 205

Leu Thr Lys Cys Gln Glu Glu Val Ser His Ile Pro Ala Val His Pro
    210                 215                 220

Gly Ser Phe Arg Pro Lys Cys Asp Glu Asn Gly Asn Tyr Leu Pro Leu
225                 230                 235                 240

```
                        Gln Cys Tyr Gly Ser Ile Gly Tyr Cys Trp Cys Val Phe Pro Asn Gly
                                        245                 250                 255
                        Thr Glu Val Pro Asn Thr Arg Ser Arg Gly His His Asn Cys Ser Glu
                                        260                 265                 270
                        Ser Leu Glu Leu Glu Asp Pro Ser Ser Gly Leu Gly Val Thr Lys Gln
                                    275                 280                 285
                        Asp Leu Gly Pro Val Pro Met
                                290                 295
```